(12) United States Patent
Knowlton et al.

(10) Patent No.: US 11,787,947 B2
(45) Date of Patent: Oct. 17, 2023

(54) DYES IN DYE AGGREGATE SYSTEMS—ENGINEERING J, K, AND DYE PACKING

(71) Applicant: Boise State University, Boise, ID (US)

(72) Inventors: William B. Knowlton, Boise, ID (US); Bernard Yurke, Boise, ID (US); Ryan D. Pensack, Boise, ID (US); Paul H. Davis, Boise, ID (US)

(73) Assignee: Boise State University, Boise, ID (US)

( * ) Notice: Subject to any disclaimer, the term of this patent is extended or adjusted under 35 U.S.C. 154(b) by 645 days.

(21) Appl. No.: 16/739,963

(22) Filed: Jan. 10, 2020

(65) Prior Publication Data

US 2020/0224035 A1 Jul. 16, 2020

Related U.S. Application Data

(60) Provisional application No. 62/790,841, filed on Jan. 10, 2019.

(51) Int. Cl.
| | |
|---|---|
| *C09B 69/10* | (2006.01) |
| *C12Q 1/68* | (2018.01) |
| *C12Q 1/6818* | (2018.01) |
| *B82Y 20/00* | (2011.01) |

(52) U.S. Cl.
CPC .......... *C09B 69/105* (2013.01); *C12Q 1/6818* (2013.01); *B82Y 20/00* (2013.01); *C12Q 2561/12* (2013.01)

(58) Field of Classification Search
CPC ..... C09B 69/105; B82Y 20/00; C12Q 1/6818; C12Q 2561/12
See application file for complete search history.

(56) References Cited

U.S. PATENT DOCUMENTS

| | | | |
|---|---|---|---|
| 9,073,962 | B2 | 7/2015 | Fracchia et al. |
| 2015/0218204 | A1 | 8/2015 | Yin et al. |
| 2017/0190573 | A1 | 7/2017 | Shen et al. |
| 2018/0044372 | A1 | 2/2018 | Han et al. |

FOREIGN PATENT DOCUMENTS

| WO | 2014018675 A1 | 1/2014 |
|---|---|---|

OTHER PUBLICATIONS

Cannon et al. J. Phys. Chem. A 2018, 122, 2086-2095. (Year: 2018).*
Cannon et al. J. Phys. Chem. A 2018, 122, 2086-2095—Supporting Information (Year: 2018).*
Tatikolov (Journal of Photochemistry and Photobiology C: Photochemistry Reviews 13, 2012, 55-90). (Year: 2012).*
Abramavicius et al., "Extracting single and two-exciton couplings in photosynthetic complexes by coherent two-dimensional electronic spectra", Chem. Phys., vol. 357(1-3), pp. 79-84, Aug. 22, 2008.
"Cadnano Turtorial Videos", http://cadnano.org/docs.html, 2 pages, accessed Apr. 16, 2020.
Cannon et al., "Coherent Exciton Delocalization in a Two-State DNA-Templated Dye Aggregate System", Journal of Physical Chemistry, vol. 121, pp. 6905-6916, Aug. 16, 2017.
Cannon et al., "Large Davydov Splitting and Strong Fluorescence Suppression: An Investigation of Exciton Delocalization in DNA-Templated Holliday Junction Dye Aggregates", Journal of Physical Chemistry, vol. 122, pp. 2086-2095, Feb. 8, 2018.
Chen, Peter C., "High Resolution Coherent 2D Spectroscopy", J. Phys. Chem. A, vol. 114, pp. 11365-11375, 2010.
Hestand et al., "Molecular Aggregate Photophysics beyond the Kasha Model: Novel Design Principles for Organic Materials", Acc. Chem. Res., vol. 50, pp. 341-350, Feb. 1, 2017.
Hestand et al., "Expanded Theory of H- and J-Molecular Aggregates: The Effects of Vibranic Coupling and Intermolecular Charge Transfer", Chem. Rev., vol. 118, pp. 7069-7163, Apr. 17, 2018.
Kumpulainen et al. "Ultralast Elementary Photochemical Processes of Organic Molecules in Liquid Solution", Chem. Rev., vol. 117, pp. 10826-10939, Dec. 13, 2016.
Marder et al., "Large Molecular Third-Order Optical Nonlinearities in Polarized Carotenoids", Science, vol. 276, pp. 1233-1237 May 23, 1997.
Wei et al., "Complex shapes self-assembled from single-stranded DNA tiles", Nature, vol. 485, pp. 623-627, May 31, 2012.
Yonggang et al., "Three-Dimensional Structures Self-Assembled from DNA Bricks", Science, vol. 338, pp. 1177-1184, Nov. 30, 2012.

* cited by examiner

*Primary Examiner* — Jezia Riley
(74) *Attorney, Agent, or Firm* — McKee, Voorhees & Sease, PLC

(57) ABSTRACT

The present disclosure is directed to designing dyes and methods to alter the parameters controlling the dipole-dipole coupling of dyes bound to a nucleotide oligomer architecture, which are used to propagate excitons for use in next generation room temperature quantum information systems. The disclosed dyes and methods are directed to changing the dye stability, symmetry, overlap, and steric hindrance of the dyes to fine tune aggregate systems.

13 Claims, 23 Drawing Sheets

|  | Ground State | Single-Excited Dye | Two Dye Singly Excited | Doubly-Excited Dye |
|---|---|---|---|---|
| Wave Function: | $\Phi_g = \Pi_m^N \phi_m^{(g)}$ | $\Phi_{e_m} = \phi_m^{(e)} \Pi_k^{k-m} \phi_k^{(g)}$ | $\Phi_{f_{em}} = \phi_m^{(e)} \phi_n^{(e)} \Pi_k^{k-m,k-n} \phi_k^{(g)}$ | $\Phi_{f_{em}} = \phi_m^{(f)} \Pi_k^{k-m} \phi_k^{(g)}$ |
| States in Terms of Ground State & Creation Operators | $\Phi_g$ | $\hat{B}_m^\dagger + \Phi_g = \Phi_{e_m}$ | $\hat{B}_m^\dagger \hat{B}_n^\dagger + \Phi_g = \Phi_{f_{mn}}$ | $2^{-1/2} \hat{B}_m^\dagger \hat{B}_m^\dagger + \Phi_g = \Phi_{f_{mn}}$ |

FIG. 1

|  | Excited Monomer | Single-Excited Dye | Two Dye Singly Excited | Doubly Excited Dye |
|---|---|---|---|---|
| Schematic of Exciton States in Dye $m$ or Dyes $m$ & $n$ or $m$ or $n$: | $S_1$ — $S_0$ | $S_2^{Sym}$ $S_1^{Asym}$ $S_0$  $m$  $n$ | $S_2$ $S_1$ $S_0$ $m$ $n$ | $S_2^{Sym}$ $S_1^{Asym}$ $S_0$ $m$ |
| Key Parameters: | $\varepsilon_m$ | $J_{m,n}, \mu_m, \mu_n$ | $K_{m,n}, \Delta d_m, \Delta d_n$ | $\Delta_m$ |
| Key Parameters in Terms of the Exciton Hamiltonian | $\varepsilon_m = (\Phi_{g_m}|\hat{H}^{(e)}|\Phi_{g_m})$ | $J_{mn} = (\Phi_{g_m}|\hat{H}^{(e)}|\Phi_{g_m})$ | $K_{mn} + \varepsilon_m + \varepsilon_n = (\Phi_{f_m}|\hat{H}^{(e)}|\Phi_{f_{mn}})$ | $\Delta m + 2 s_m = (\Phi_{f_m}|\hat{H}^{(e)}|\Phi_{f_{mn}})$ |

FIG. 2

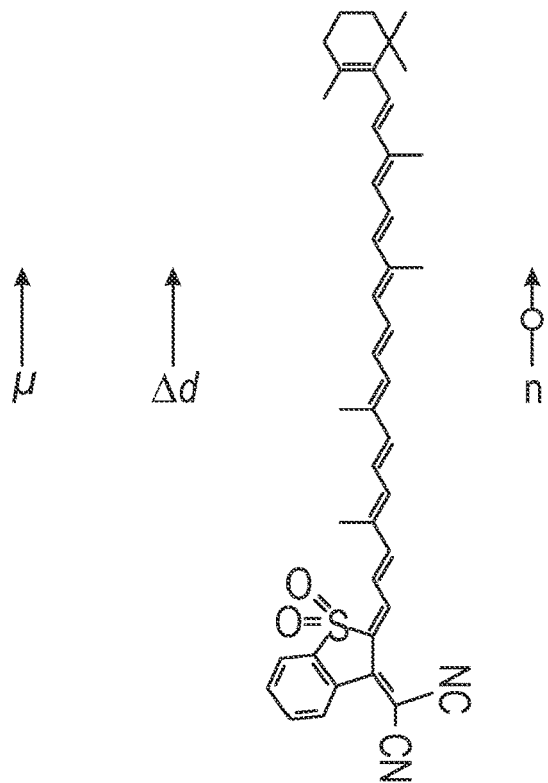
FIG. 4A
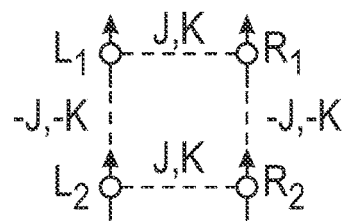
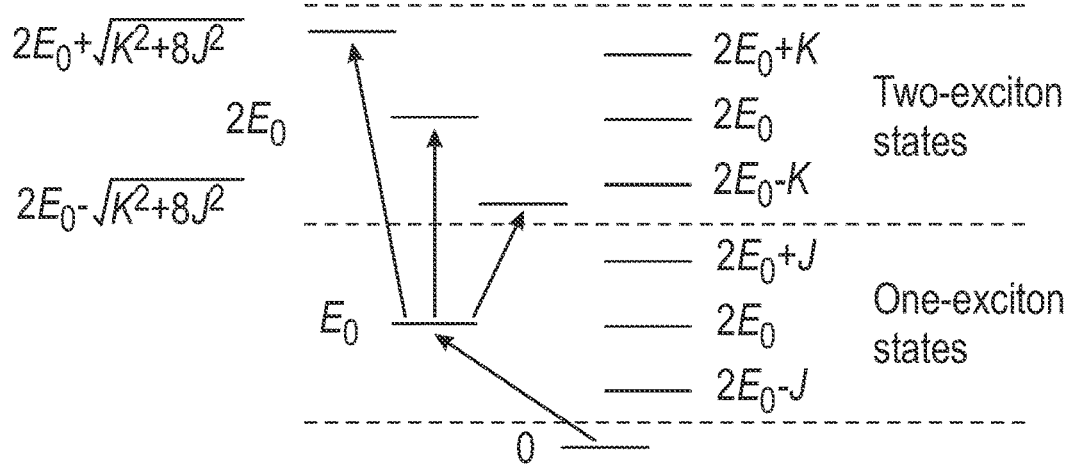
FIG. 4B

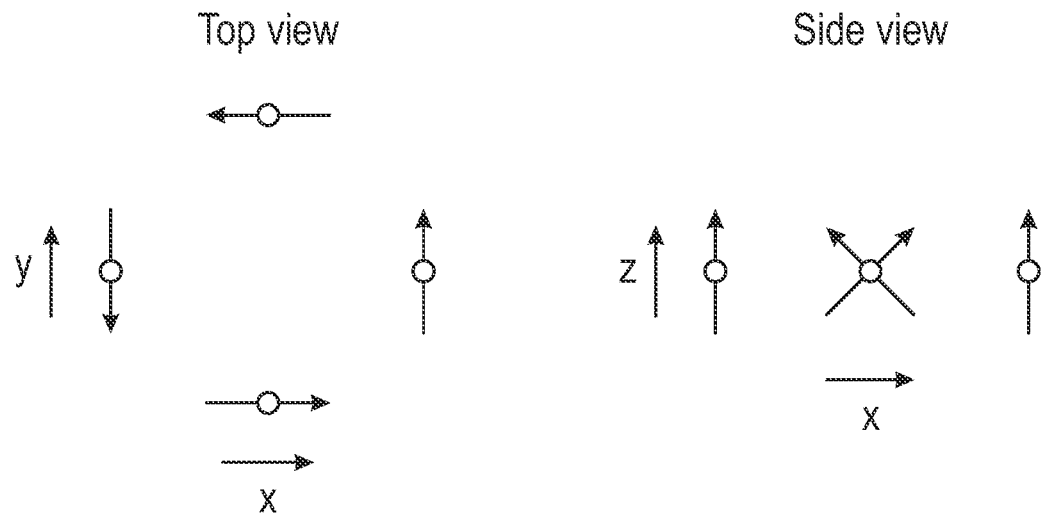
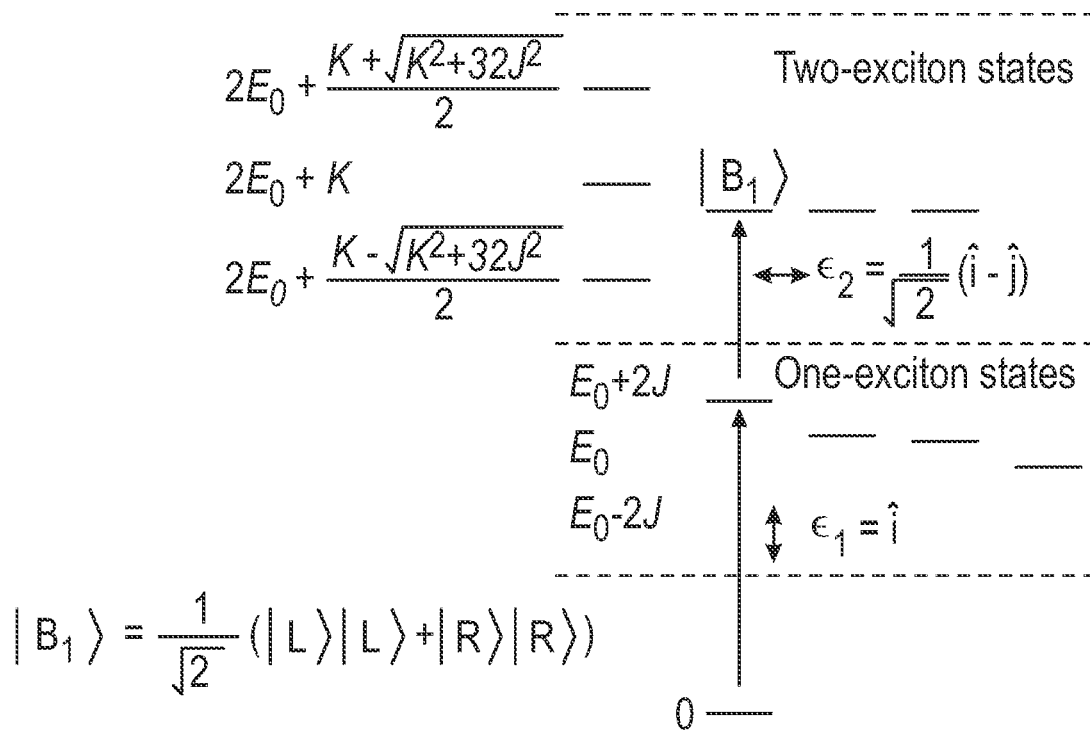
FIG. 4C

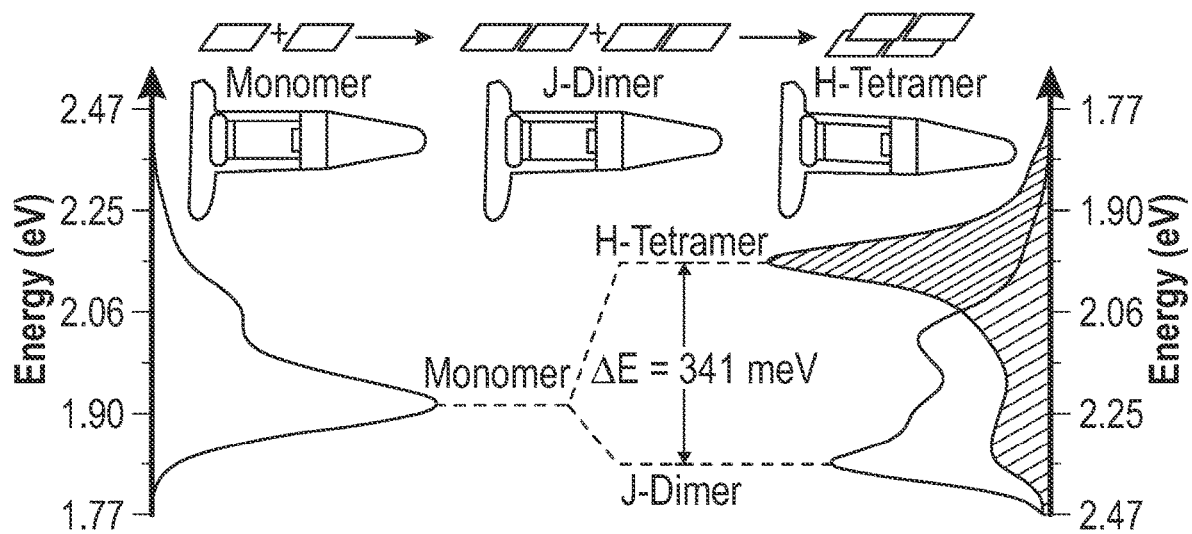
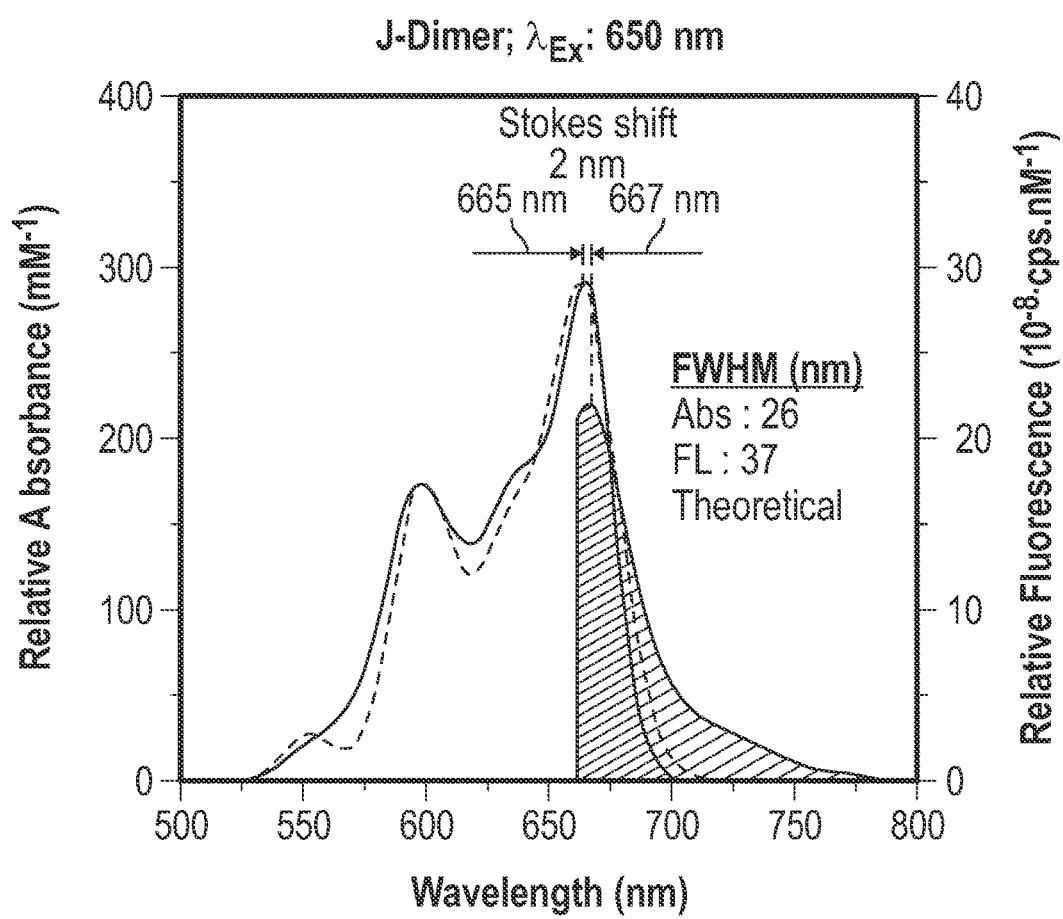
FIG. 5A

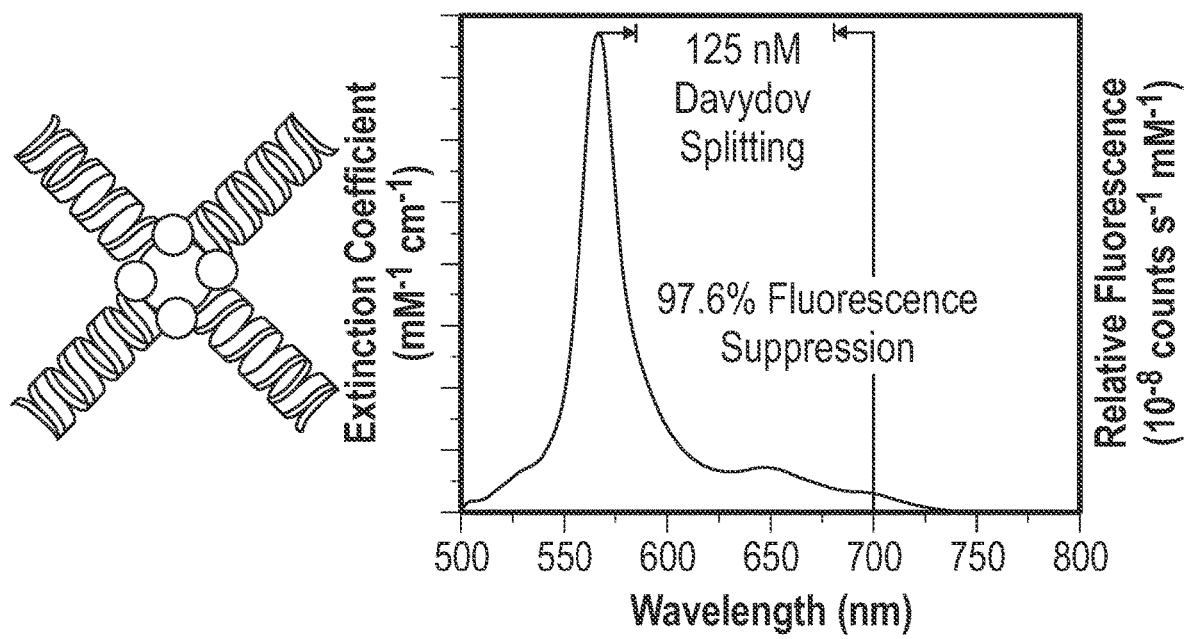
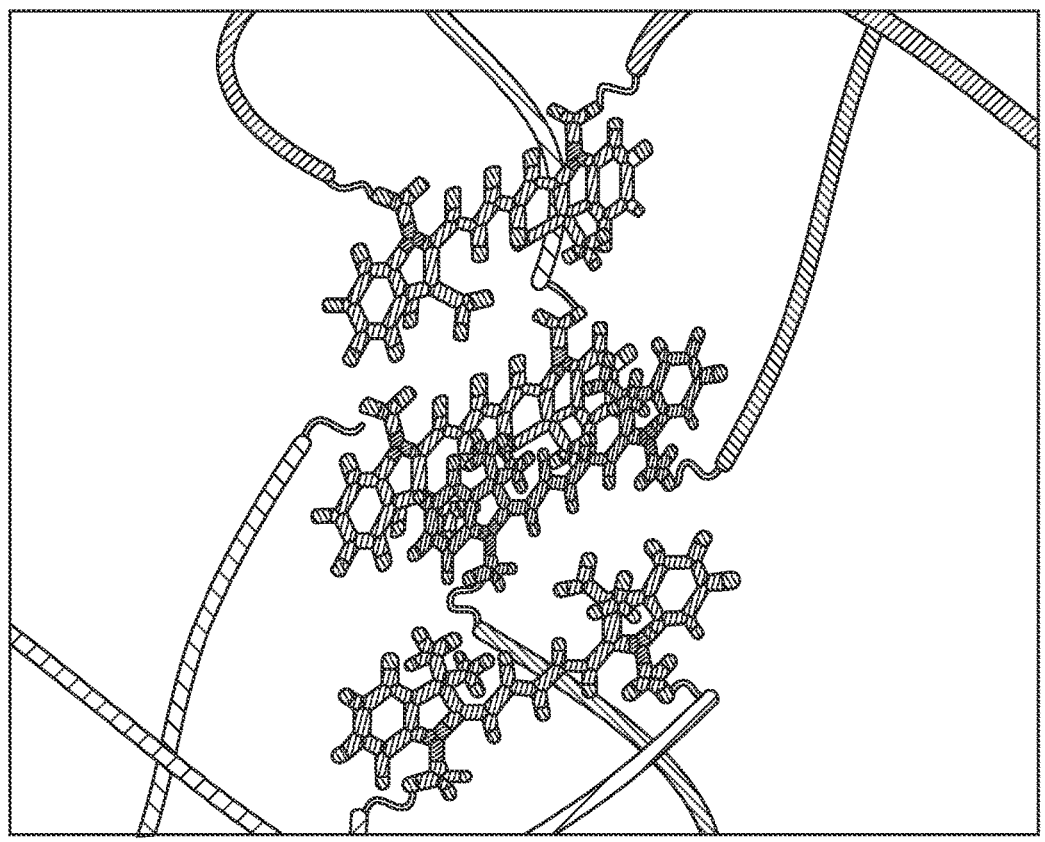
FIG. 5B

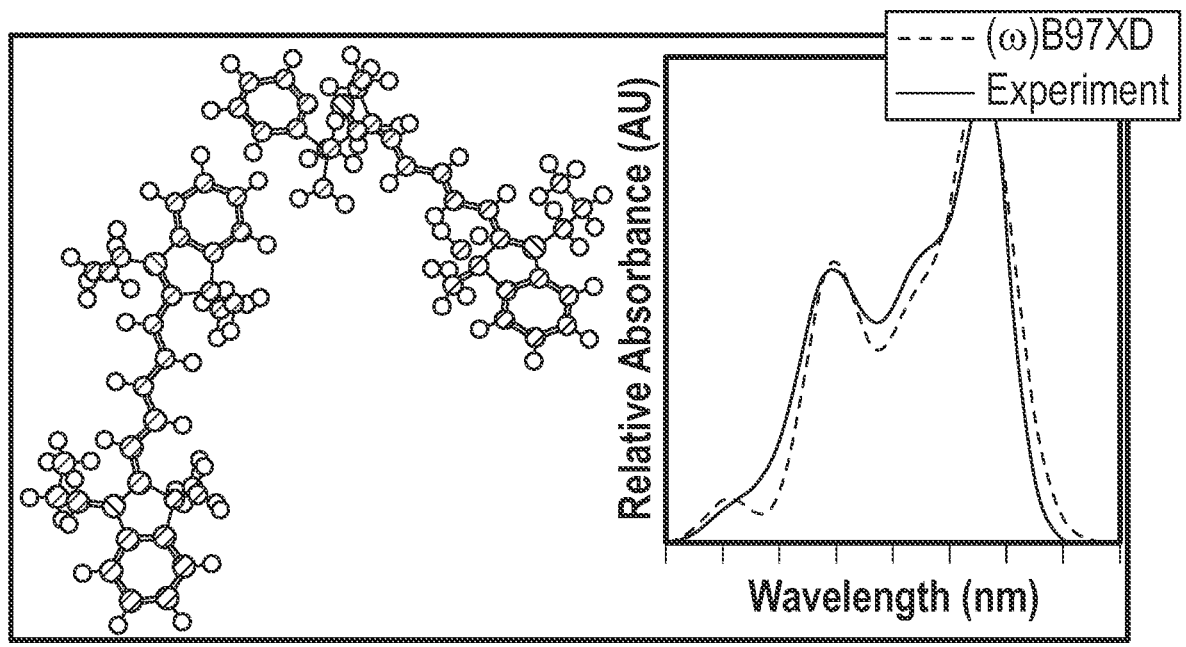
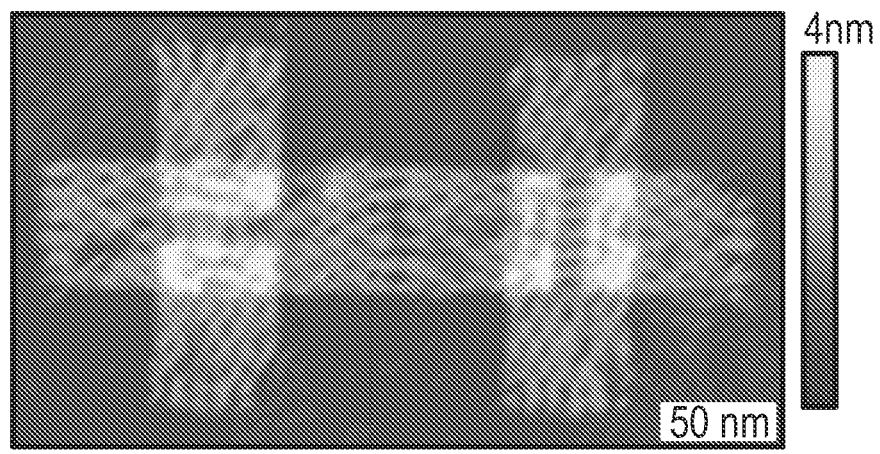
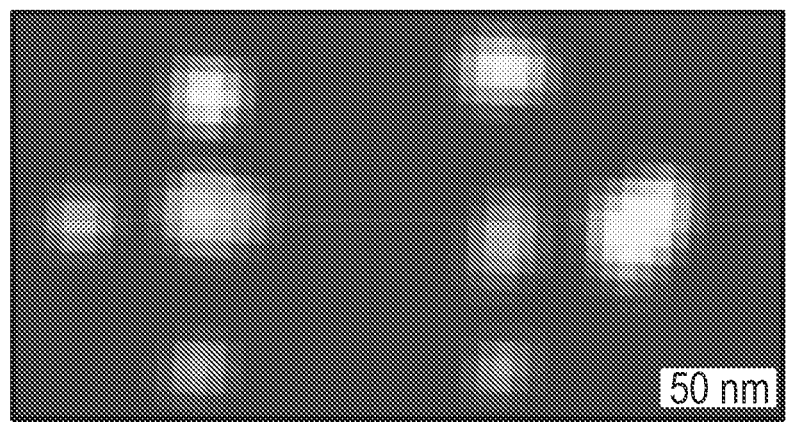
FIG. 5C

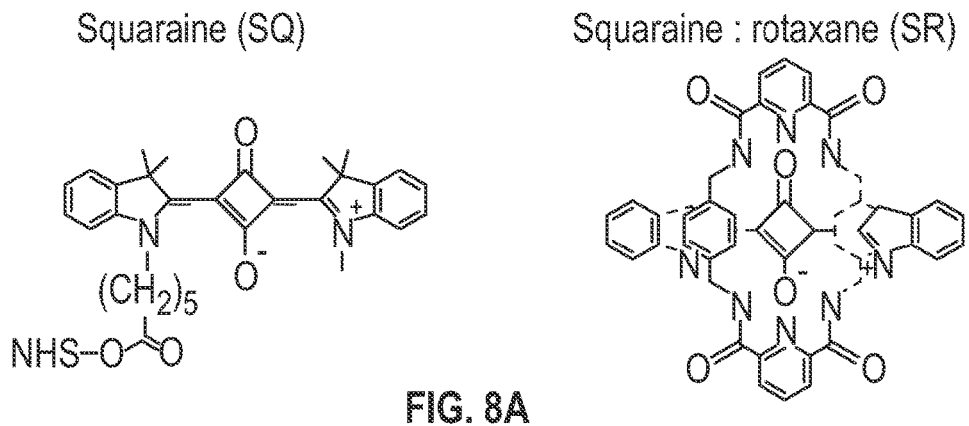
FIG. 8A
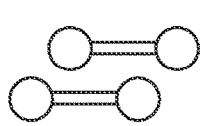
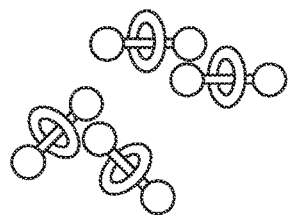
FIG. 8B
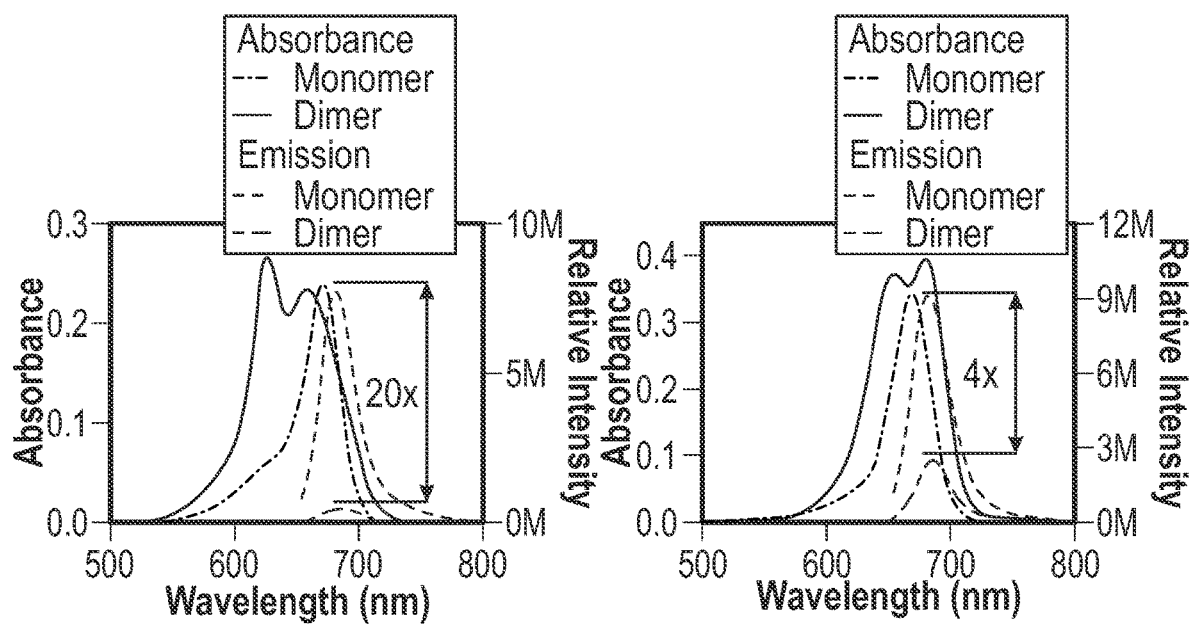
FIG. 8C
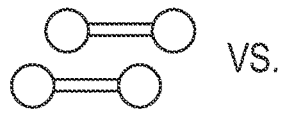 vs. 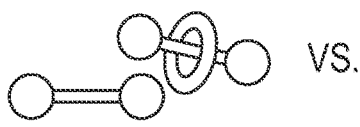 vs. 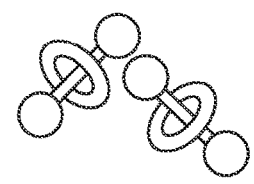
FIG. 8D

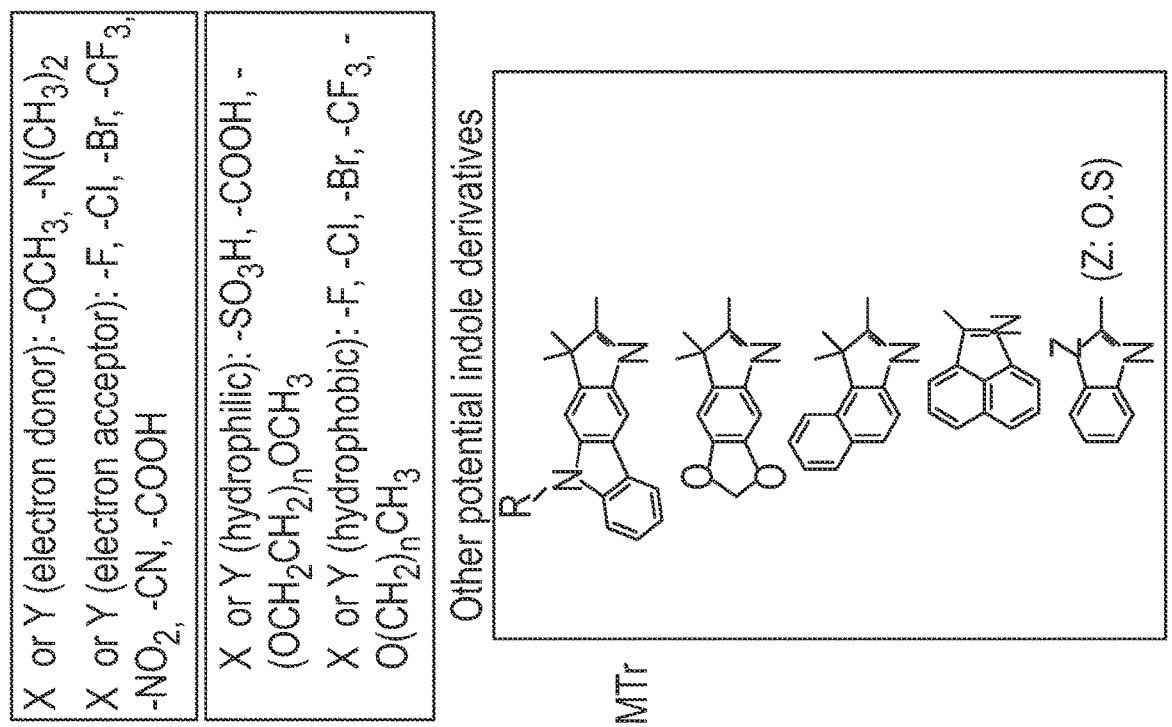
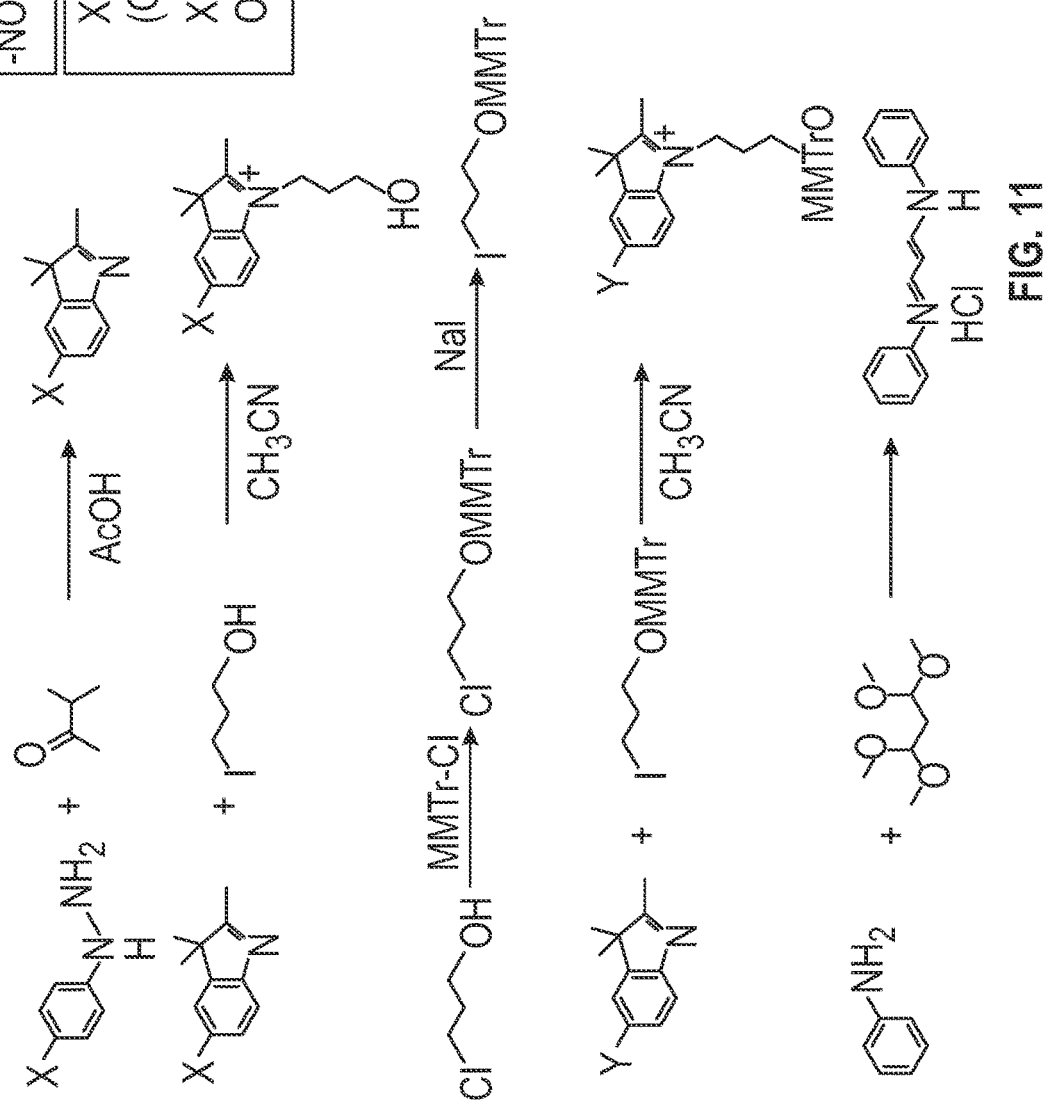
FIG. 11

DYES IN DYE AGGREGATE SYSTEMS—ENGINEERING J, K, AND DYE PACKING

CROSS REFERENCE TO RELATED APPLICATION

The present application claims priority to the earlier filed U.S. Provisional Application having Ser. No. 62/790,841, filed Jan. 10, 2019, and hereby incorporates subject matter of the provisional application in its entirety.

GRANT REFERENCE

This invention was made with government support under the U.S. Department of Energy award number DE-SC0020089. The government has certain rights in the invention.

FIELD OF THE INVENTION

The invention relates generally to quantum computing. More specifically, the invention relates to designing dyes to alter the parameters controlling the coupling of dyes bound to a nucleotide oligomer architecture, which are used to propagate excitons for use in next generation room temperature quantum information systems.

BACKGROUND OF THE INVENTION

Recent observations of Frenkel exciton quantum coherence and delocalization in natural light harvesting dye aggregate complexes of photosynthetic organisms have fueled substantial interest in simulating and controlling this behavior for next generation room temperature quantum information systems (QIS). However, it is needed to ascertain if dye aggregates can be designed to control Frenkel exciton delocalization and quantum coherence which will enable quantum entanglement.

In Frenkel exciton theory, exciton delocalization and quantum coherence are mediated by transition dipole ($\mu$) interactions leading to a transition or nonpermanent dipole-dipole coupling, described by the parameter J, between dyes that enable the excitons to spread in a wave-like manner over an aggregate of optically excited dyes (i.e., chromophores or fluorophores). Static (i.e., permanent) dipole-dipole interactions that arise from the difference between a dye's ground and excited state static dipoles ($\Delta d$) leading to a permanent dipole coupling between dyes, described by the parameter K. Static dipole-dipole coupling gives rise to two body exciton interactions that contribute to nonlinear optical responses and it is this combination of exciton delocalization and exciton-exciton interactions that gives rise to entangled many-exciton states and the ability to envision excitonic quantum gates. Jct (ct=charge transfer) is the coupling between dyes related to the overlap of the wavefunctions in the conjugated system.

By controlling the parameters J, Jct, and K, it will be possible to achieve room temperature molecular excitonic quantum computing using rational designs of excitonic quantum gates composed of pre-configured dyes that are templated and organized through nucleic acid self-assembly. Over the last 10 years, work has been conducted toward understanding the conditions that are conducive to exciton delocalization and quantum coherence, minimizing decoherence, and promoting coherent excitation dynamics over timescales required to enable quantum computing.

However, how to control exciton quantum entanglement via exciton delocalization and exciton-exciton interaction through parameters J, Jct, and K to adjust dipole-dipole interactions, especially the less well studied parameter K, has yet to be achieved Accordingly, it is an objective of the present disclosure to methods of altering the parameters of J and K.

These and other objects, advantages and features of the present disclosure will become apparent from the following specification taken in conjunction with the claims set forth herein.

BRIEF SUMMARY OF THE INVENTION

Disclosed herein are dyes (i.e. chromophores and fluorophores) and methods of controlling the physical parameters J, Jct, and K for tuning DNA-templated dye networks, which forms a system of Frenkel (molecular) excitons.

In one aspect, disclosed herein are dyes and methods for controlling J, wherein J can be tuned by dyes that have a large extinction coefficient, thus shielding the emitting part of the dye, which will increase dye stability, can lead to large extinction coefficients. In another aspect, reducing the vibronic effects, see below, will lead to greater extinction coefficients, wherein the vibronic effect is reduced by sing multiple linkers from the dye to attach to the DNA scaffold and/or using shorter linkers to increase the extinction coefficient.

In another aspect, disclosed herein are dyes and methods for controlling K, wherein K can be altered by changing dyes symmetry, wherein K may be increased by increasing the asymmetric. In another aspect, K may be decreased by making a dye more symmetrical. The more asymmetry, the greater the static (permanent) dipole moment.

In still another aspect, disclosed herein are dyes and methods for controlling Jct (ct=charge transfer) by altering the coupling between dyes related to the overlap of the wavefunctions in the conjugated system, wherein the distance between the adjacent dyes and their relative displacement controls the coupling is altered. In one aspect, Jct is lowered by increasing the steric hindrance of adjacent dyes. In another aspect, Jct is increased by lowering the steric hindrance of adjacent dyes.

In a further aspect, disclosed herein are dyes and methods for controlling the vibronic effects, wherein reducing the vibronic effects (e.g., smaller vibronic shoulders in the absorption data and sharper peaks) leads to greater extinction coefficients (i.e., good absorber), brighter (i.e., minimize nonradiative transfer—see below), and more stable (i.e., less reactive dye). Less reactive dyes (thus more stable, longer lifetime) can be achieved by adding functional groups that protect the reactive part of the dye (e.g., steric hindrance, see below).

In another aspect, disclosed herein are dyes and methods for controlling exciton lifetimes: By minimizing the vibronic impact in and on dye aggregates, the exciton lifetime increases. Steric hindrance between dyes decreases dye movement or sliding against one another. Hence, altering the steric hindrance of dyes (e.g., adjust/modify functional groups), the exciton lifetime will be adjusted. In another aspect, conical insertions occurrences are minimized by adjusting the electrostatics (dielectric constants) rather than using viscosity; The dielectric constant is inversely proportional the exciton lifetime, so by tuning the dielectric constant, the occurrence of conical intersections can be tuned.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

BRIEF DESCRIPTION OF THE DRAWINGS

FIG. 1 shows three level site basis states.

FIG. 2 shows Frenkel excitation Hamiltonian energies and excitation energy schematics.

FIG. 4A schematic representation of a linear dye molecule with a polar π-bond system. The dye's transition dipole vector μ and the difference Δd between the ground state and excited state static dipole vectors are nearly parallel to the long axis of the molecule. Here, rod-shaped molecules are represented as an arrow with a dot in the center. The arrow represents the orientation vector n a unit vector parallel to the long axis of the molecule. FIG. 4B is a schematic representation of a dye aggregate having both J stacking (dyes stacked head-to-tail) and H stacking (dyes stacked face-to-face) and the associated energy level diagram. FIG. 4C is a schematic representation of a chiral dye aggregate and its associated energy level diagram with allowed one photon optical transitions (bright states) and not allowed transitions (dark states) for specific incoming light polarizations $\epsilon_1$ and $\epsilon_2$. Hence, some entangle states can be optically accessed while the dark states cannot and the entangled states can be tuned with a specific polarization.

FIG. 5A top is a graphical representation of a Large Davydov splitting (~2J) apparent in J-dimer and H-tetramer aggregate structures constructed on duplex DNA causing substantial color change; FIG. 5A bottom is a graphical representation the J-dimer absorption and emission spectra (black) modeled with KRM model analysis tool (dashed green); FIG. 5B top is a graphical representation a H-tetramer constructed on DNA Holliday junction showing larger Davydov splitting and substantial fluorescence suppression; FIG. 5B bottom is a graphical representation the predicted dye configuration of the tetramer using in-house KRM model analysis tool; FIG. 5C top left is a schematic representation of the DFT optimized Cy5 dimer; FIG. 5C top right is a graphical representation of the comparison of absorbance data (black) with the prediction (blue) of the KRM model analysis tool with input from DFT calculations; FIG. 5C middle is a pictorial representation of the AFM image of DNA origami cross-tile structure used to perform super-resolution imaging; FIG. 5C bottom is a pictorial representation of super-resolution image with 14 nm lateral optical resolution.

FIG. 8A is a schematic representation of the general SQ and SR chemical structure. FIG. 8B is a schematic representation of the proposed dye packing for SQ and SR. FIG. 8C is a graphical representation of the absorption spectra of monomers and DNA-templated SQ and SR dimer aggregates. FIG. 8D is a schematic representation of the hypothetical dye packing with increasing no. of rotaxane rings (steric bulk).

FIG. 11 is a schematic representation of a synthetic scheme to obtain symmetric and asymmetric Cy5 dyes with substituents to alter hydro-phobic (-philic) and polarity.

DETAILED DESCRIPTION

Figure 3:
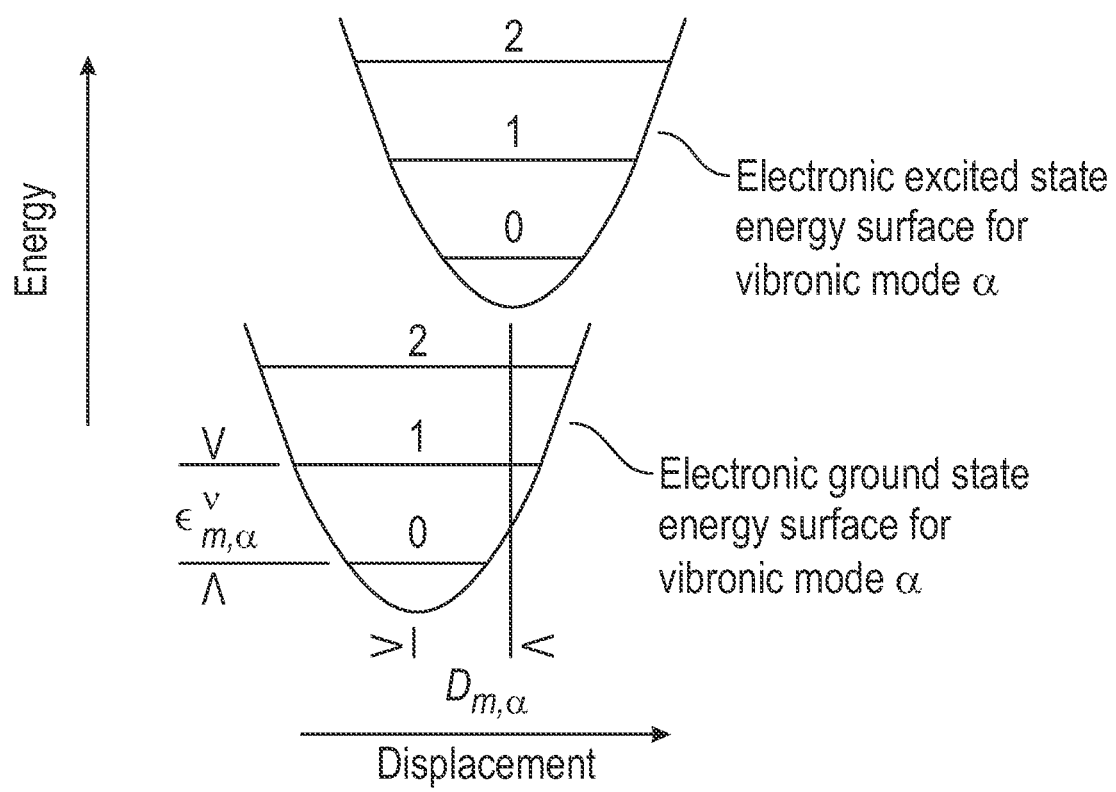
FIG. 3 is a graphical representation of the quantities $\varepsilon_{m,\alpha}^v$ and $D_{m,\alpha}$ for vibronic mode $\alpha$ of dye m.

In the following detailed description, reference may made to the accompanying drawings, schemes, and structures which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). The embodiments of this disclosure are not limited to any specific compositions and methods which can vary and are understood by skilled artisans. It is further to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (i.e. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (i.e., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, 6, or more substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (i.e., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (i.e., cyclopropyl, cyclopentyl, cyclohexyl, cycloheptyl, cyclooctyl, etc.), branched-chain alkyl groups (i.e., isopropyl, tert-butyl, sec-butyl, isobutyl, etc.), and alkyl-substituted alkyl groups (i.e., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, aryl carbonyloxy, alkoxycarbonyloxy, aryloxy, aryloxycarbonyloxy, carboxylate, alkylcarbonyl, arylcarbonyl, alkoxycarbonyl, aminocarbonyl, alkyl aminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

The term "ester" as used herein refers to —$R^{30}COOR^{31}$ group. $R^{30}$ is absent, a substituted or unsubstituted alkylene, cycloalkylene, alkenylene, alkynylene, arylene, aralkylene, heterocyclylalkylene, or heterocyclylene group as defined herein. $R^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —$R^{32}NR^{33}R^{34}$ groups. $R^{32}$ is absent, a substituted or unsubstituted alkylene, cycloalkylene, alkenylene, alkynylene, arylene, aralkylene, heterocyclylalkylene, or heterocyclylene group as defined herein. $R^{33}$ and $R^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of $R^{32'}NR^{33'}R^{34'}$ groups, wherein $R^{32''}$ $R^{33'}$, and $R^{34}$ are independently hydrogen, or a substituted or unsubstituted alkyl, cycloalkyl, alkenyl, alkynyl, aryl, aralkyl, heterocyclylalkyl, or heterocyclyl group as defined herein. The term "alcohol" as used herein refers to —$R^{35}OH$ groups. $R^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —$R^{36}COOH$ groups. $R^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —$R^{37}OR^{38}$ groups. $R^{37}$ is absent, a substituted or unsubstituted alkylene, cycloalkylene, alkenylene, alkynylene, arylene, aralkylene, heterocyclylalkylene, or heterocyclylene group as defined herein. $R^{38}$ is a substituted or unsubstituted alkyl, cycloalkyl, alkenyl, alkynyl, aryl, aralkyl, heterocyclylalkyl, or heterocyclyl group as defined herein.

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Oligonucleotides

The dyes disclosed herein are tethered to one, two or more oligonucleotides, at least one of which comprises a donor, acceptor, and one or more photochromic nucleotides. As used herein, an oligonucleotide can contain all the natural nucleotides found in nature or one, more, or all modified or synthetic nucleotides, in addition to the natural nucleotides and the nucleotides containing the donor, acceptor, or photochromic moiety. A modified or synthetic nucleotide in the oligonucleotides can differ from a natural occurring nucleotide in its base, sugar, and/or backbone moiety.

The oligonucleotide disclosed herein can be, but are not limited to, a peptide nucleic acid (PNA), a locked nucleic acid (LNA), an unlocked nucleic acid (UNA), a bridged nucleic acid polymer, or combination thereof.

PNA is an artificially synthesized polymer like DNA or RNA. While DNA and RNA have a deoxyribose and ribose sugar backbone, respectively, PNA's backbone is composed of repeating N-(2-aminoethyl)-glycine units linked by peptide bonds. The various purine and pyrimidine bases are linked to the backbone by a methylene bridge (—CH2-) and a carbonyl group (—(C=O)—).

PNA oligomers can show greater specificity in binding to complementary DNAs, with a PNA/DNA base mismatch being more destabilizing than a similar mismatch in a DNA/DNA duplex.

A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules. LNA polymer are synthesized chemically and are commercially available. The locked ribose conformation enhances base stacking and backbone pre-organization. This significantly increases the hybridization properties (melting temperature) of oligonucleotides.

Bridged nucleic acids (BNAs) are modified RNA nucleotides. They are sometimes also referred to as constrained or inaccessible RNA molecules. BNA monomers can contain a five-membered, six-membered, or even a seven-membered bridged structure with a "fixed" C3'-endo sugar puckering. The bridge is synthetically incorporated at the 2', 4'-position of the ribose to afford a 2', 4'-BNA monomer. The monomers can be incorporated into oligonucleotide polymeric structures using standard phosphoamidite chemistry. BNAs are structurally rigid oligo-nucleotides with increased binding affinities and stability.

The oligonucleotide as used herein can be a DNA strand containing mainly natural or modified A, T, C, G nucleotide, and/or derivative thereof. The oligonucleotide can also be RNA strand containing mainly natural or modified A, U, C, G nucleotide, and/or derivative thereof. The oligonucleotide can be a mixed strand containing any of natural or modified A, U, C, T, and G nucleotide.

A modified nucleotide can be, but is not limited to, d5SICS and dNaM that base pair with each other and dTPT3 also base pairs with dNaM (Floyd Romesberg), 2-amino-8-(2-thienyl)purine that base-pairs with pyridine-2-one (y), 7-(2-thienyl)imidazo[4,5-b]pyridine (Ds) that base-pairs with pyrrole-2-carbaldehyde (Pa), and Ds that base pairs with 4-[3-(6-aminohexanamido)-1-propynyl]-2-nitropyrrole (Px).

The oligonucleotide can be a single strand, which one or more dyes and can fold into such a conformation, so that the dyes are close enough to each other, so a photochromic Förster resonance energy transfer (pcFRET) can happen between the dyes.

As used herein, Forster resonance energy transfer (FRET), fluorescence resonance energy transfer (FRET), resonance energy transfer (RET), or electronic energy transfer (EET) refers to energy transfer between two light-sensitive molecules, such as between two or more dyes, such as a fluorophore or a chromophore. A first dye, initially in its electronic excited state, may transfer energy to a second dye through nonradiative dipole-dipole coupling. The efficiency of this energy transfer is inversely proportional to the sixth power of the distance between the first and second dye.

The DNA or RNA structure may be a duplex including two or more mostly matching or complementary oligonucleotides. In this situation, one of the two or more oligonucleotides can contain one of or all the dyes, and the other can contain the rest.

In some embodiments, two or more oligonucleotides forms one duplex. In some embodiments, two or more oligonucleotides forms two or more duplexes.

Nucleotide Architecture

Nucleotide nanotechnology can be used to form complicated one-, two-, and three-dimensional architectures. The nucleotide architectures may comprise of one or more nucleotide bricks. The nucleotide bricks are designed to use the Watson-Crick pairing of the nucleotides to cause the bricks to self-assemble into the final and predictable architectures. Any method of designing the architectures and self-assembly may be used, such as but not limited to nucleotide origami, nucleotide brick molecular canvases, single stranded tile techniques, or any other method of nucleotide folding or nanoassembly such as, but not limited to, using nucleotide tiles, nucleotide scaffolds, nucleotide lattices, four-armed junction, double-crossover structures, nanotubes, static nucleotide structures, dynamically changeable nucleotide structures, or any other synthetic biology technique (as described in U.S. Pat. No. 9,073,962, U.S. Pub. No.: US 2017/0190573, U.S. Pub. No.: US 2015/0218204, U.S. Pub. No.: US 2018/0044372, or International Publication Number WO 2014/018675, each of which is incorporated by reference).

The nucleobase making up the bricks may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tetramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivatives at positions 2, 3, and 4, and fluoro derivates at position 2 and 3; purine/pyrimidine mimics, such as but not limited to azole hetercyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or theino pyridiones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or $N^6$-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2-oxophenoxazine, pyrrolo-dC and derivatives, 3-MI, 6-MI, 6-MAP, or furan-modified bases.

Non-limiting examples of nucleotide analogs include, but are not limited to, phosporothioate nucleotides, 2'-O-methyl ribonucleotides, 2'-O-methoxy-ethyl ribonucleotides, peptide nucleotides, N3'-P5' phosphoroamidate, 2'-fluoro-arabino nucleotides, locked nucleotides, morpholino phosphoroamidate, cyclohexene nucleotides, tricyclodeoxynucleotides, or triazole-linked nucleotides.

The nucleotides can then be polymerized into oligomers. The design of the oligomers will depend on the design of the final architecture. Simple architectures may be designed by any methods. However, more complex architectures may be design using software such as, but not limited to, caDNAno (as described at http://cadnano.org/docs.html, and herein incorporated by reference), to minimize errors and time. The user may input the desired shape of the architecture into the software and once finalized, the software will provide the oligomer sequences of the bricks to create the desired architecture.

In some embodiments the architecture is comprised of nucleotide brick molecular canvases, wherein the canvases are made of 1 to 5,000 nucleotide bricks comprising of nucleotide oligomers of 24 to 48 nucleotides and will self-assemble in a single reaction, a "single-pot" synthesis, as described in U.S. Pub. No.: US 2015/0218204. In more preferable embodiments, the canvases are made of 1 to 1,000 nucleotide bricks, from 1 to 750 nucleotide bricks, from 1 to 500 nucleotide bricks, or from 1 to 250 nucleotide bricks. In other embodiments, the oligomers comprise of 24 to 42 nucleotides, from 24 to 36 nucleotides, or from 26 to 36 nucleotides.

In another embodiment the architecture is made step wise using a serial fluidic flow to build the final shape as described in U.S. Pat. No. 9,073,962.

In some embodiments, the architecture is assembled using the origami approach. With a DNA origami approach, for example, a long scaffold nucleic acid strand is folded to a predesigned shape through interactions with relatively shorter staple strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome. In some embodiments the number of staple strands is less than about 500 staple strands, less than about 400 staple strands, less than about 300 staple strands, less than about 200 staple strands, or less than about 100 staple strands.

In some embodiments, the architecture is assembled from single-stranded tiles (SSTs) (see, e.g., Wei B. et al. Nature 485: 626, 2012, incorporated by reference herein) or nucleic acid "bricks" (see, e.g., Ke Y. et al. Science 388:1177, 2012; International Publication Number WO 2014/018675 A1 each of which is incorporated by reference herein). For example, single-stranded 2- or 4-domain oligonucleotides self-assemble, through sequence-specific adhering, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

In some embodiments, the architecture is made from a single stranded oligomer, as described in U.S. Pub. No.: 2018/0044372 and herein incorporated by reference. A single strand of DNA used for assembling a nanostructure in accordance with the present disclosure may vary in length. In some embodiments, a single strand of DNA has a length of 500 nucleotides to 10,000 nucleotides, or more. For example, a single strand of DNA may have a length of 500 to 9000 nucleotides, 500 to 8000 nucleotides, 500 to 7000 nucleotides, 500 to 6000 nucleotides, 500 to 5000 nucleotides, 500 to 4000 nucleotides, 500 to 3000 nucleotides, 500 to 2000 nucleotides, 500 to 1000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a single strand of DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides.

In some embodiments, the architecture is two-dimensional and comprises a single layer of bricks or a single scaffold. The single layer of bricks may form a molecular canvas. In other embodiments, the architecture is three-dimensional and may contain 2, 3, 4, 5, 6, 7, 8, 9, 10, 20, 30, or more layers of two-dimensional structures depending on the desired final shape.

In some embodiments, the architecture is attached to a substrate, such as a glass slide, a silicon base, or a breadboard.

In other embodiments, the architecture remains in a solution.

Dyes

A dye may be any fluorophore or chromophore. A fluorophore absorbs light energy of a specific wavelength and re-emits light at a longer wavelength. A chromophore is any chemical group that produces a color when it absorbs energy. As used herein, the terms "dye," "chromophore," and "fluorophore" may be interchangeable unless otherwise indicated. The absorbed wavelength, energy transfer efficiency, and time before emission of a specific dye depend on both the dye structure and its chemical environment, as the dye in its excited state interacts with surrounding molecules. Wavelengths of maximum absorption excitation) and emission (for example, Absorption/Emission=485 nm/517 nm) are the typical terms used to refer to a given fluorophore, but the whole spectrum may also be important for consideration. The excitation wavelength spectrum may be a very narrow or broader band, or it may be all beyond a cutoff level. The emission spectrum is usually sharper than the excitation spectrum, has a longer wavelength, and has correspondingly lower energy. Excitation energy of a fluorophore can range from ultraviolet through the visible spectrum, and emission energy can continue from visible light into the near infrared region.

Fluorophores typically contain several combined aromatic groups, or planar or cyclic molecules with several $\pi$ bonds. A fluorophore that can be used in the all-optical switches disclosed herein is typically an organic small molecule of 20-100 atoms and has a molecular weight of from about 200 Da to about 1000 Da. In some embodiments, the fluorophore used as a donor or acceptor can have a molecular weight of from about 100 Da to about 2,000 Da, from about 300 Da to about 800 Da, from about 400 Da to about 600 Da, about 350 Da, about 400 Da, about 450 Da, about 500 Da, about 550 Da, or any value there between.

A fluorophore that can be used herein include, but is not limited to, a xanthene derivatives such as fluorescein, rhodamine, Oregon green, eosin, and Texas red; cyanine derivatives such as cyanine, indocarbocyanine, oxacarbocyanine, thiacarbocyanine, and merocyanine; a squaraine derivative or ring-substituted squaraines such as Seta, SeTau, and Square dyes; a naphthalene derivative such as a dansyl or prodan derivative; a coumarin derivative; a oxadiazole derivative such as pyridyloxazole, nitrobenzoxadiazole and benzoxadiazole; an anthracene derivatives such as anthraquinones including DRAQS, DRAQ7 and CyTRAK Orange; a pyrene derivative such as cascade blue; an oxazine derivative such as Nile red, Nile blue, cresyl violet, oxazine 170; an acridine derivative such as proflavin, acridine orange, acridine yellow; and an arylmethine derivative such as auramine, crystal violet, and malachite green; a tetrapyrrole derivative such as porphin, phthalocyanine, and bilirubin.

A fluorophore disclosed herein may further include, but is not limited to, a trademarked dye, such as a CF dye (Biotium); DRAQ or CyTRAK probes (BioStatus); BODIPY (Invitrogen); Alexa Fluor (Invitrogen); DyLight Fluor (Thermo Scientific, Pierce); Atto and Tracy (Sigma Aldrich); FluoProbes (Interchim); Abberior Dyes (Abberior); DY and MegaStokes Dyes (Dyomics); Sulfo Cy dyes (Cyandye); HiLyte Fluor (AnaSpec); Seta, SeTau and Square Dyes (SETA BioMedicals); Quasar and Cal Fluor dyes (Biosearch Technologies); SureLight Dyes (APC, RPEPerCP, Phycobilisomes)(Columbia Biosciences); APC, APCXL, RPE, BPE (Phyco-Biotech, Greensea, Prozyme, Flogen); or Vio Dyes (Miltenyi Biotec).

The fluorophore can be tethered or covalently attached to a nucleotide of the oligonucleotide(s) or can be intercalated within the oligonucleotides. The dyes are preferably attached through a tether to the DNA. The fluorophore can have one or more tethers. Increasing the number of tethers or decreasing the length of the tether will restrict the movement of the dye. This restriction may result in increased sterics between dyes. The dye may be tethered at a single or multiple location. The dye may have 1, 2, 3, 4, 5, 6, or more tethers. The tethers may be positioned along the dye at opposite ends or on the same end. The dye may be tethered to one or more nucleic acids.

In some embodiments, a dye disclosed herein include, but is not limited to, Afro 390 dye, Eterneion 384/480 dye, DEAC (D-AMCA) dye, or a derivative thereof, which can be obtain from companies including IDT and Biosynthesis.

In some embodiments, the dye is an Alexa or ATTO 488 dye such as 6-FAM dye and Fluorescein dT dye, which can be obtain from companies including IDT and Biosynthesis. The donor and acceptor can be chosen once the photochromic moiety of the specific all-optical switch and its corresponding wavelength are established.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Frenkel Molecular Excitation Theory and Corresponding Key Parameters

The physical parameters J and K can be tuned using DNA-templated dye networks, which forms a system of Frenkel (molecular) excitons. The details and significance of these physical parameters are discussed in the following. Insight to these physical parameters is best gleaned by defining the following aspects of the Frenkel Model, which describes a system of Frenkel (molecular) excitons: (1) the single-molecule energy eigenstates, (2) the multi-exciton Hilbert space, and (3) the Frenkel Hamiltonian governing the system.

Single-Molecule Energy Eigenstates

By way of nonlimiting example, given an aggregate comprised of N three-level dyes in which only interactions between pairs of dyes are considered (i.e., between the dye at site m and the dye at site n). The single dye energy eigenstates are represented by three wave functions (FIG. 1): (1) the ground state wave function here taken to be a singlet state, $\phi_m^{(g)}$, (2) the singly excited state wave function, here taken to be the lowest singlet state, $\phi_m^{(e)}$, and (3) the double-excited state wave function, here taken to be the next higher singlet state, $\phi_m^{(f)}$ where m denotes the dye at site m. Invoking the Heitler-London approximation the ground state of the aggregate is given by a direct product of the ground states of all dyes, $\Phi_g$, and the single-exciton basis is constructed by replacing one of the dye ground states by its excited state and is given by $\Phi_{e_m}$. The wave functions are shown in FIG. 1.

Multi-Exciton Hilbert Space

Note that exciton states that exhibit exciton delocalization are created by the interaction of two (or more) strongly coupled dyes resulted in excited states that are split (i.e., Davydov splitting) as compared to the monomer state (see schematics in FIG. 2). Focusing on dye dimer aggregates, the exciton states can be described by two-exciton basis states that come in two forms: dyes (m) that are doubly excited ($\Phi_{f_{mn}}$), and two dyes (m & n) that are singly excited ($\Phi_{f_{mn}}$) which are shown in FIG. 1. This model contains N singly excited states and M=N(N+1)/2 doubly-excited states. An approximation is often made for the states where a dye molecule is doubly excited are excluded. This is the hard-core boson approximation (i.e., two excitons cannot reside on the same dye). Inclusion of these states, as done here, constitutes the soft-boson approximation (i.e., two excitons can reside on the same dye). Schematics of the exciton energy states are shown in FIG. 2.

Frenkel Hamiltonian Governing a System of Frenkel (Molecular) Excitons

The behavior of Frenkel excitons is well approximated by an augmented Frenkel Hamiltonian that includes (see FIG. 2) exciton exchange energies $J_{m,n}$ (i.e., a single exciton nonpermanent dipole-dipole coupling between dyes on sites m and n) leading to resonant exciton hopping; and the exciton-exciton interaction energies $K_{m,n}$ (permanent dipole-dipole coupling between two excitons, one each on dye sites m and n). Both $J_{m,n}$ and $K_{m,n}$ are key parameters that we propose that can be harnessed to create, study, and control exciton quantum entanglement. An augmented Frenkel Hamiltonian of this form is given by:

$$\hat{H}^{(e)} = \sum_m \varepsilon_m^e \hat{B}_m^\dagger \hat{B}_m + \sum_{m,n}^{m \neq n} J_{m,n} \hat{B}_m^\dagger \hat{B}_n + \qquad (1)$$

$$\frac{1}{2}\sum_{m,n}^{m \neq n} K_{m,n} \hat{B}_m^\dagger \hat{B}_m \hat{B}_n^\dagger \hat{B}_n + \frac{1}{2}\sum_{m,n}^{m \neq n} \Delta_m \hat{B}_m^\dagger \hat{B}_m^\dagger \hat{B}_m \hat{B}_m.$$

where $\varepsilon_m^e$ is the monomer transition energy of a single excited dye (excited monomer: S0→S1) on the m site, $\hat{B}_m^\dagger$ is the bosonic exciton creation operator on site m, and $\hat{B}_m$ is the bosonic exciton annihilation operator on site m. $K_{m,n}$ is related to the average energy of two singly excited dyes (see FIG. 2), given by:

$$\varepsilon_{f,mn}^e = \langle \Phi_{f,mn} | \hat{H}^{(e)} | \Phi_{f,mn} \rangle = \varepsilon_m^e + \varepsilon_n^e + K_{mn}. \qquad (2)$$

Similarly, $\Delta_m$ is related to the average energy of a doubly excited dye:

$$\varepsilon_{f,mm}^e = \langle \Phi_{fmm} | \hat{H}^{(e)} | \Phi_{fmm} \rangle = 2\varepsilon_m^e + \Delta_m. \qquad (3)$$

Eqn. 3 does not describe three exciton states or higher.

Dipole Approximation and Define $J_{m,n}$, $K_{m,n}$ and $\Delta d$

When intermolecular distances are greater than dye size, the dipole approximation for molecular charge densities can be further invoked such that the $J_{m,n}$ and $K_{m,n}$ couplings can be expressed in dipole-dipole interaction form. $J_{m,n}$ becomes the intermolecular dipole-dipole interaction between the molecular transition dipoles, µm and µn, for the dyes at sites m and n, which is given by:

$$J_{m,n} = \frac{1}{4\pi\varepsilon\varepsilon_o}\left(\frac{\mu_m \cdot \mu_n}{|R_{m,n}|^3} - 3\frac{(\mu_m \cdot R_{m,n})(\mu_n \cdot R_{m,n})}{|R_{m,n}|^5}\right) \quad (4)$$

where $R_{m,n}$ is the vector connecting dyes at sites m and n. $K_{m,n}$ involves the difference between the excited state and ground state static (i.e., permanent) dipoles, $\Delta d_m$ and $\Delta d_n$, also known as the difference dipoles, for the dyes at site m and n, and is given by:

$$K_{m,n} = \frac{1}{4\pi\varepsilon\varepsilon_o}\left(\frac{\Delta d_m \cdot \Delta d_n}{|R_{m,n}|^3} - 3\frac{(\Delta d_m \cdot R_{m,n})(\Delta d_n \cdot R_{m,n})}{|R_{m,n}|^5}\right) \quad (5)$$

and thus $K_{m,n}$, is zero for a molecule without a static dipole moment (e.g., a symmetric dye, $\Delta d=0$). Although Eqns. 4 and 5 provide straightforward expressions to give an indication of the parameters on which they depend, for intermolecular distances that are less than the dye size (i.e., the dipole-dipole approximation fails), more accurate expressions for $J_{m,n}$ and $K_{m,n}$ are necessary and are used in the KRM Model Analysis tool (see B. L. Cannon, D. L. Kellis, L. K. Patten, P. H. Davis, J. Lee, E. Graugnard, B. Yurke and W. B. Knowlton, Coherent exciton delocalization in a two-state DNA-templated dye aggregate system, The Journal of Physical Chemistry A, 121 (37), 6905-6916 (2017) and B. L. Cannon, L. K. Patten, D. L. Kellis, P. H. Davis, J. Lee, E. Graugnard, B. Yurke and W. B. Knowlton, Large davydov splitting and strong fluorescence suppression: An investigation of exciton delocalization in DNA-templated holliday junction dye aggregates, The Journal of Physical Chemistry A, 122 (8), 2086-2095 (2018), herein incorporated by reference in their entirety) based on the Kühn-Renger-May (KRM) model used to fit absorbance and circular dichroism data. Density functional theory (DFT) and TD-DFT also produces more accurate expressions for $J_{m,n}$ and $K_{m,n}$.

The Hamiltonian for Vibrons

The augmented Frenkel Hamiltonian expression (Eqn. 1) does not include the coupling effects of the vibronic quanta (i.e., vibrons) to the excitons of the system. The Hamiltonian, a Holstein-like Hamiltonian, for the vibrons and their coupling to the excitons can be expressed as:

$$\hat{H}^{(v)} = \sum_m \sum_\alpha \varepsilon_{m,\alpha}^v \hat{A}_{m,\alpha}^\dagger \hat{A}_{m,\alpha} + \sum_m \sum_\alpha D_{m,\alpha} \hat{B}_m^\dagger \hat{B}_m \left(\hat{A}_{m,\alpha}^\dagger + \hat{A}_{m,\alpha}\right) \quad (6)$$

where $\hat{A}_{m,n}^\dagger$ is the vibron creation operator, $\hat{A}_{m,n}$ is the vibron annihilation operator, $\varepsilon_{m,n}^v$ is the corresponding vibron energy, and $D_{m,n}$ is the displacement parameter between the electronic ground state and the electronic excited state harmonic oscillator potentials—all for vibronic mode α on the dye at site m. The meaning of $\varepsilon_{m,n}^v$ and $\varepsilon_{m,n}^v$ is illustrated schematically in FIG. 3 where $\varepsilon_{m,n}^v$ is the difference in energy between two neighboring vibronic energy states while $D_{m,n}$ is the difference between the electronic ground and excited state minimums. The sum of Eqns. 1 and 6 gives an augmented Frenkel Hamiltonian, or Frenkel-Holstein Hamiltonian, that includes vibronic effects on excitons and is given by:

$$\hat{H} = \hat{H}^{(e)} + \hat{H}^{(v)} \quad (7)$$

$$= \sum_m \varepsilon_m^e \hat{B}_m^\dagger \hat{B}_m + \sum_{m,n}^{m\neq n} J_{m,n} \hat{B}_m^\dagger \hat{B}_n + \frac{1}{2}\sum_{m,n}^{m\neq n} K_{m,n} \hat{B}_m^\dagger \hat{B}_n^\dagger \hat{B}_m \hat{B}_n +$$

$$\frac{1}{2}\sum_{m,n}^{m\neq n} \Delta_m \hat{B}_m^\dagger \hat{B}_m^\dagger \hat{B}_m \hat{B}_m + \sum_m \sum_\alpha \varepsilon_{m,\alpha}^v \hat{A}_{m,\alpha}^\dagger \hat{A}_{m,\alpha} +$$

$$\sum_m \sum_\alpha D_{m,\alpha} \hat{B}_m^\dagger \hat{B}_m \left(\hat{A}_{m,\alpha}^\dagger + \hat{A}_{m,\alpha}\right)$$

Key Parameters

Both $J_{m,n}$ and $K_{m,n}$ along with their associated parameters can be used to create and control exciton quantum entanglement and used to construct excitonic quantum gates. Hence, the strength of coupling between dyes m and n—in which one dye is singly excited (one exciton), both dyes are excited singly excited (two exciton), or one dye is doubly excited (two excitons) and the orientation of the dyes relative to one another—is critically important to exciton quantum entanglement and quantum computing. Super-resolution microscopy and spectroscopy, atomic force microscopy (AFM) and metrology of DNA origami, (see FIG. 5C, middle and bottom) which may be used to quantify the precision with which dye orientation can be controlled using DNA.

From Eqn. 4, we see that $J_{m,n}$ is related to the transition dipole moments, $\mu_m$ and $\mu_n$, of dyes m an n, which are parallel to the incident electromagnetic (EM) field inducing and oscillating the dipoles. The square of a single dye's transition dipole, $\mu m^2$, is proportional to the extinction coefficient. These relationships indicate that dyes with larger extinction coefficients will yield aggregates with larger $J_{m,n}$. $J_{m,n}$ can be determined from the amount of Davydov splitting (~$2J_{m,n}$ for dimers) obtained from steady state absorption and by using the KRM Model analysis tool.

From Eqn. 5, $K_{m,n}$ is proportional to the change in excited and ground state static (permanent) dipole moments, $\Delta d_m$ and $\Delta d_n$ of dyes m and n. $K_{m,n}$ can be determined using ultrafast nonlinear spectroscopy, while $\Delta d_m$ can be obtained using Stark spectroscopy. Another key parameter is the excitonic coherence lifetime $\tau_c$. $\tau_c$ is related to the number of times an exciton can be coherently exchanged between dyes:

$$n = J_{m,n}\tau_c c \quad (8)$$

where c is the speed of light, and $J_{m,n}$ is expressed in units of wavenumber (cm$^{-1}$). While it can be difficult to measure $\tau_c$ directly, $\tau_c$ is related to the absorption spectral width, $\Delta E$, of the optical transitions associated with the excitonic coherence, which can be readily measured via steady state absorption. Spectral narrowing in the form of a reduced $\Delta E$, for example, is an optical signature of exciton delocalization. Such spectral narrowing can be manifested in the form of either motional narrowing (i.e., reduction of homogeneous broadening) or exchange narrowing (i.e., reduction of inhomogeneous broadening). $\Delta E$ in the form of homogeneous broadening is related to the intrinsic time scale τc over which excitonic quantum coherence decays. Ultrafast nonlinear spectroscopy (ensemble construct measurement) and super-resolution imaging (single construct measurement) are needed to disentangle the various homogeneous and inhomogeneous broadening contributions to ΔE and better understand the fundamental mechanisms responsible for the dephasing of the excitonic coherence $\tau_c$.

Mathematical/Theoretical Reasoning

Equation 1 shows that J and K are separate and not related. J is dependent on the transition dipole moment and K is dependent on the static dipole moment. Additional terms can be added to the Hamiltonian including a term for vibronic effects and for charge transfer.

Approach for Engineering J

Related to the transition dipole moment, J can potentially be tuned by dyes that have a large extinction coefficient, thus shielding the emitting part of the dye, which will increase dye stability, can lead to large extinction coefficients. Reducing the vibronic effects (see Vibronic Effects below) will lead to greater extinction coefficients. Using multiple linkers from the dye to attach to the DNA scaffold and shorter linkers should reduce vibronic effects and increase the extinction coefficient.

Approach for Engineering K

Related to the static dipole moment, K can be tuned by creating dyes that are highly asymmetric. The more asymmetry, the greater the static (permanent) dipole moment.

Approach for Engineering Jct

Jct (ct=charge transfer) is the coupling between dyes related to the overlap of the wavefunctions in the conjugated system. The distance between the adjacent dyes and their relative displacement controls the coupling. The greater the constructive overlap of the wavefunctions, the stronger the Jct. In general, the greater the steric hindrance, the less Jct. Hence, if the steric hindrance between the two adjacent dyes can be controlled, then Jct can be controlled or tuned.

Approach for Engineering $\Delta_m$

Δ is the anharmonic parameter that characterizes quartic exciton coupling within the same dye (as opposed to quartic couplings between dyes associated with K). Denoting the energy difference between the $m^{th}$ dye's ground state and its first optically excited state as $\varepsilon_m^e$, the energy of two excitons occupying the same dye is $2\varepsilon_m^{e+\Delta_m}=2U_{mm,mm}$. Δ is a property of the dye and can only be changed by changing the dye species or the chemical structure of the dye. Depending on the application, it is advantageous for Δ to be positive, negative, or zero. Δ modifies the energy of two excitons or excitations on the same site and may only affect the two-exciton manifold. For example, for devices such as exciton beam-splitters or exciton phase-shifters that are expected to exhibit linear behavior even when more than one exciton is present, it is desirable for Δ to be zero. Controlled quantum gates can be constructed by employing either the Δ or K nonlinearity, but if the nonlinearity Δ is used for this application it is desirable that $|\Delta| \geq |J|$.

Approach for Engineering Vibronic Effects

Reducing the vibronic effects (e.g., smaller vibronic shoulders in the absorption data and sharper peaks) leads to greater extinction coefficients (i.e., good absorber), brighter (i.e., minimize nonradiative transfer—see below), and more stable (i.e., less reactive dye). Less reactive dyes (thus more stable, longer lifetime) can be achieved by adding functional groups that protect the reactive part of the dye (e.g., steric hindrance—see below).

Approach for Engineering Longer Exciton Lifetimes

By minimizing the vibronic impact in and on dye aggregates, the exciton lifetime should increase. Steric hindrance between dyes should decrease dye movement or sliding against one another. Hence, if the steric hindrance of dyes can be modified/tuned (e.g., adjust/modify functional groups), the exciton lifetime should be adjustable. Additionally, minimize the occurrence of conical intersections. This may be done by adjusting the electrostatics (dielectric constants) rather than using viscosity; The dielectric constant is inversely proportional the exciton lifetime, so by tuning the dielectric constant, the occurrence of conical intersections can be tuned.

EXAMPLES

Example 1—Enhancing $J_{m,n}$

In pursuit of a methodology to increase $J_{m,n}$, attempts to change dye-dye orientation, which directly influences dipole-dipole coupling between dyes were pursued. This approach was carried out by varying the ionic strength (i.e., salt concentration) of the solution. The dye Cy5 was chosen for the study due to its large extinction coefficient (~250,000 M-1 cm-1), thus a large transition dipole moment, which should enhance $J_{m,n}$. Duplex DNA and both mobile and immobile DNA Holliday junction scaffolds were used to organize the Cy5 dyes. Holliday junctions are four-armed DNA junctions that are larger than dsDNA. Holliday junctions are a convenient way in which to bring two (dimer), three (trimer) and four dyes (i.e., tetramers) within ~1-2 nm to form an aggregate.

Figure 5D:
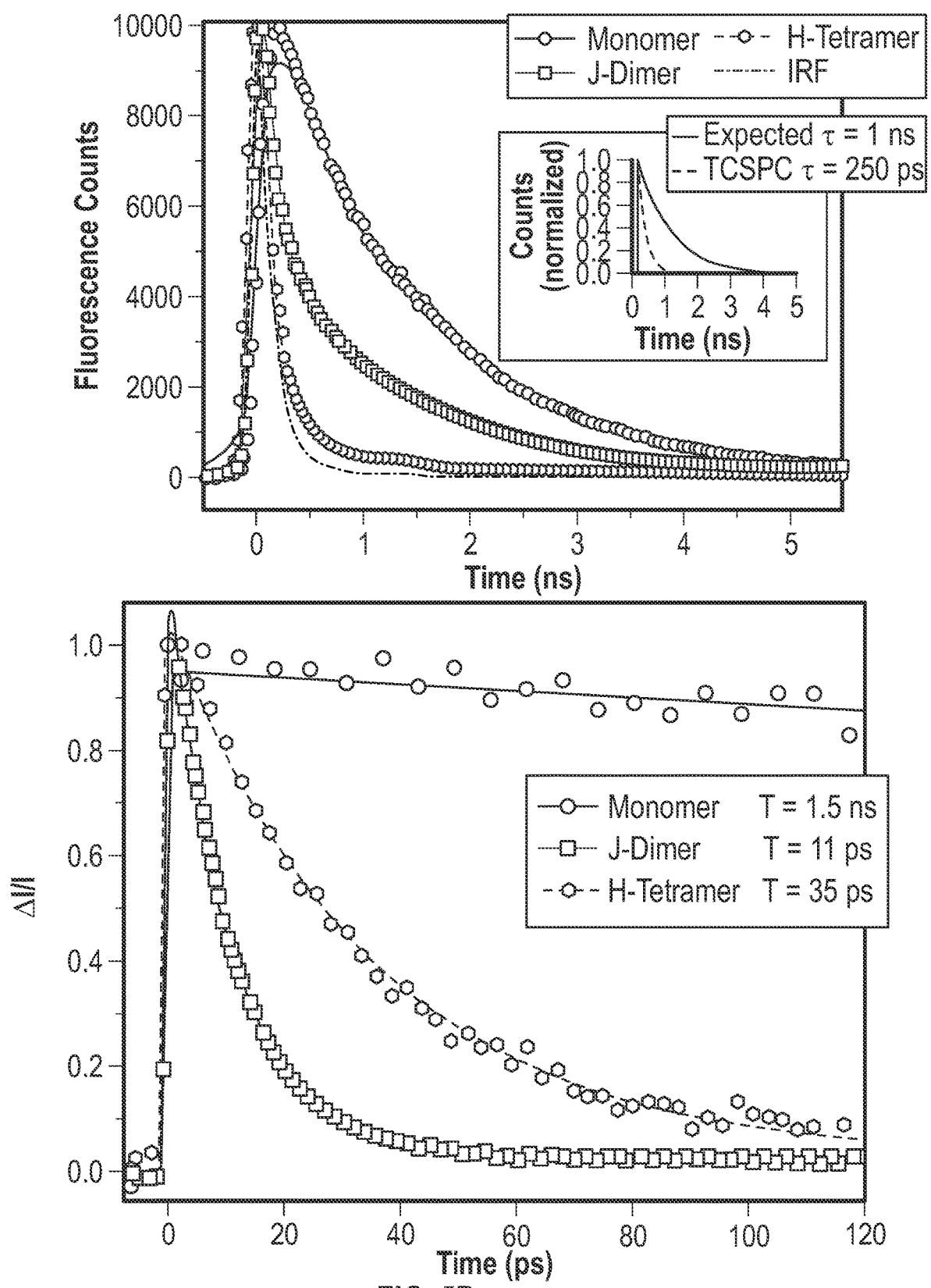
FIG. 5D is a graphical representation of the ultrafast time-resolved fluorescence (top) and transient absorbance (bottom) measurements of J-dimers and H-tetramers.
Figure 6A:
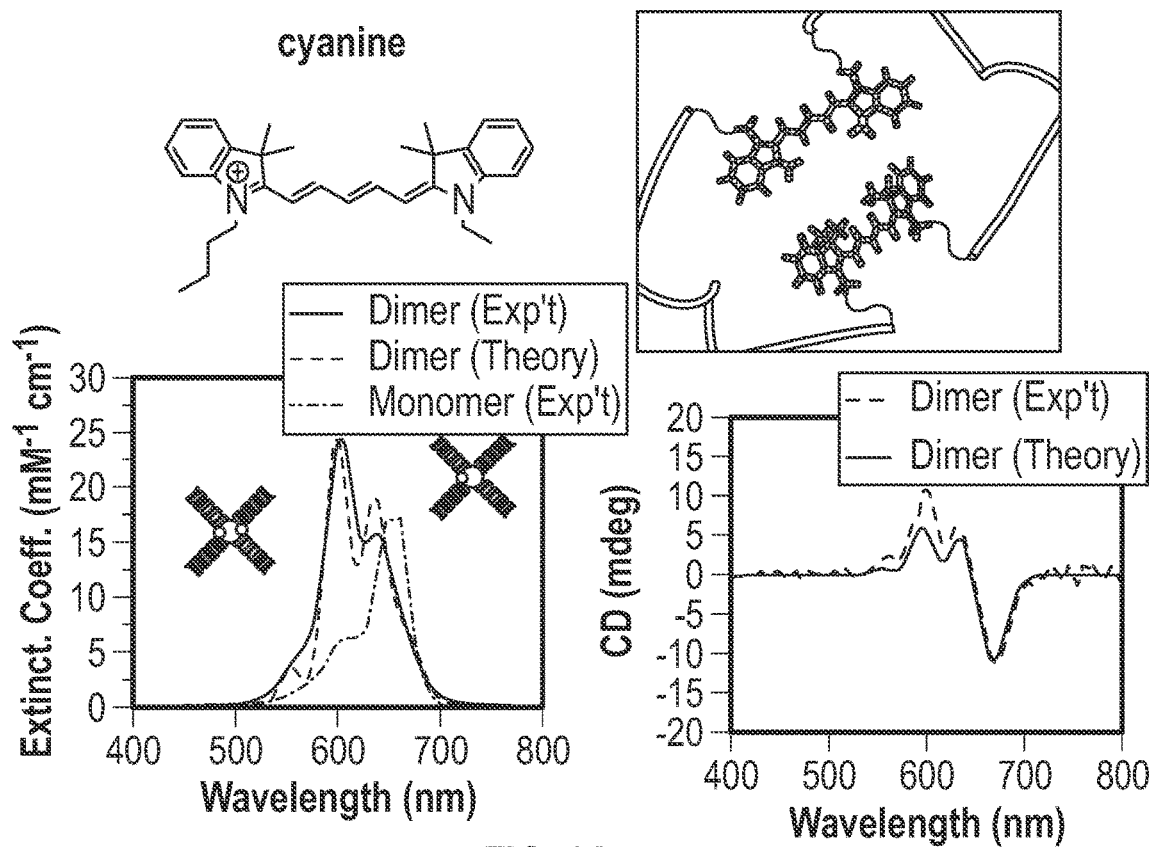
FIG. 6A is a schematic and graphical representation showing counterclockwise from top left the general chemical structure, monomer and aggregate absorption spectra, including KRM model fit, aggregate CD spectrum (incl. KRM model fit), and corresponding structure for Cy5 dimer aggregate. The dimer aggregates have been templated via an immobile DNA Holliday junction.
Figure 6B:
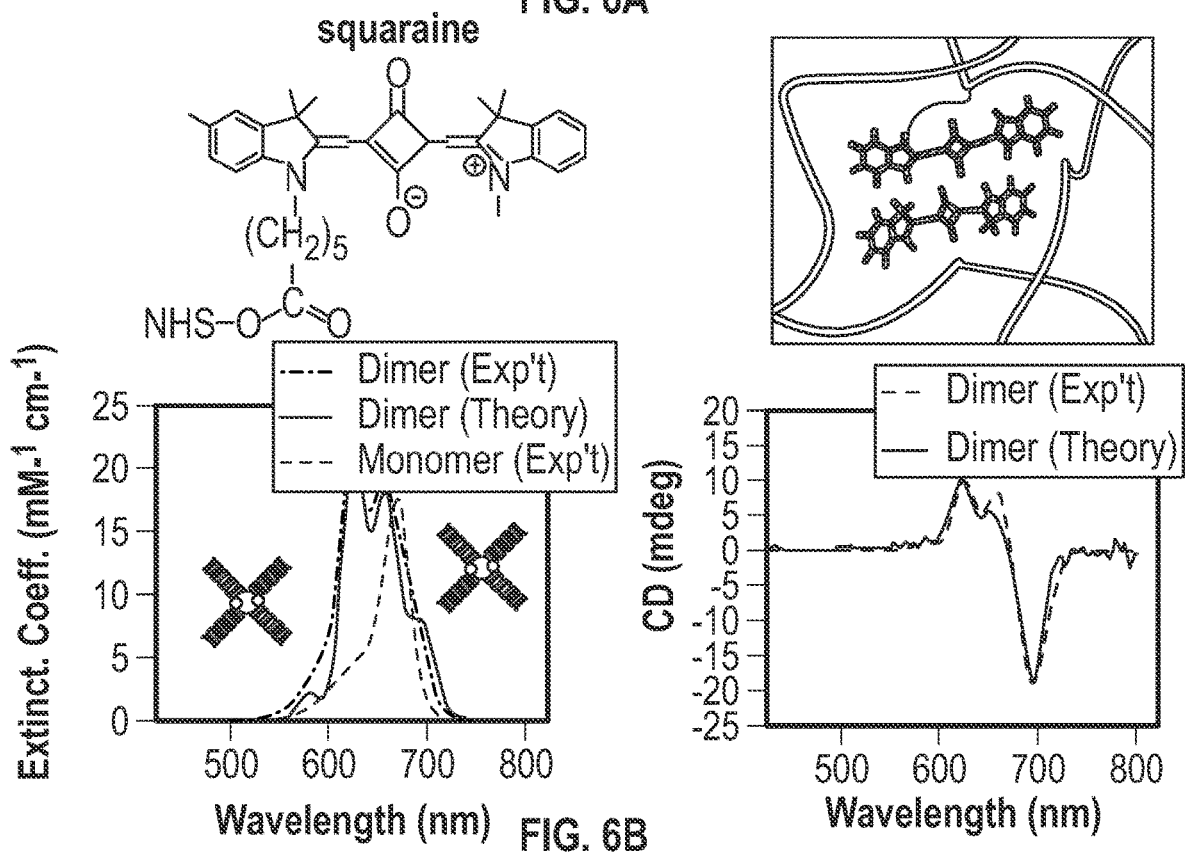
FIG. 6B is a schematic and graphical representation showing counterclockwise from top left the general chemical structure, monomer and aggregate absorption spectra, including KRM model fit, aggregate CD spectrum (incl. KRM model fit), and corresponding structure for Squaraine-660-NHS

The Cy5 dyes were assembled into dye aggregates including several dimers, trimers, and tetramers. Signatures of exciton delocalization—including J- and H-aggregate behavior, spectral (exchange) narrowing (i.e., decreased ΔE), and Davydov splitting—were sufficiently large to induce vivid color changes. Both the mobile and immobile DNA Holliday junction templated tetramer aggregates exhibited significant Davydov splitting (mobile: ~100 nm, ~340 meV; immobile: ~125 nm, ~400 meV). The Davydov splitting of immobile DNA Holliday junction template tetramer aggregates is the largest reported within the literature (FIGS. 5A-B) and an order of magnitude greater than seen by others for Cy3 dimers. The immobile DNA Holliday junction templated tetramer configuration also exhibited the greatest fluorescence suppression (97.6% as compared to the monomer) when the H-like peak was excited (FIG. 5B).

Example 2—KRM Modeling

We have developed and implemented an in-house analysis program (termed KRM model analysis tool) based on the KRM Frenkel Hamiltonian to simultaneously fit absorbance and circular dichroism (CD) data. From the fitting, this model extracts the configuration of the dyes within an aggregate (FIGS. 5A and 5B—bottom). We have used the KRM modeling tool, DFT, and TD-DFT to describe dimer aggregate behavior (FIG. 5C, top).

Example 3—Parameter J

DNA templating is a powerful way to control dye packing it can be used to bring molecules within 3 Å of one another. Yet, there are few studies in this field attempting to control dye packing on an even finer, e.g., sub-Å, scale. As $J_{m,n}$ is inversely proportional to the cube of the distance between the dyes, we postulate that promoting dense dye packing will increase $J_{m,n}$. Dense dye packing can be achieved by promoting favorable intermolecular interactions between dyes and inhibiting such interactions between the dyes and their environment. Intermolecular interactions are embodied by dye structural properties such as hydrophobicity, electronic factors (which include dipolar and dispersion forces), and sterics.

Figure 7:
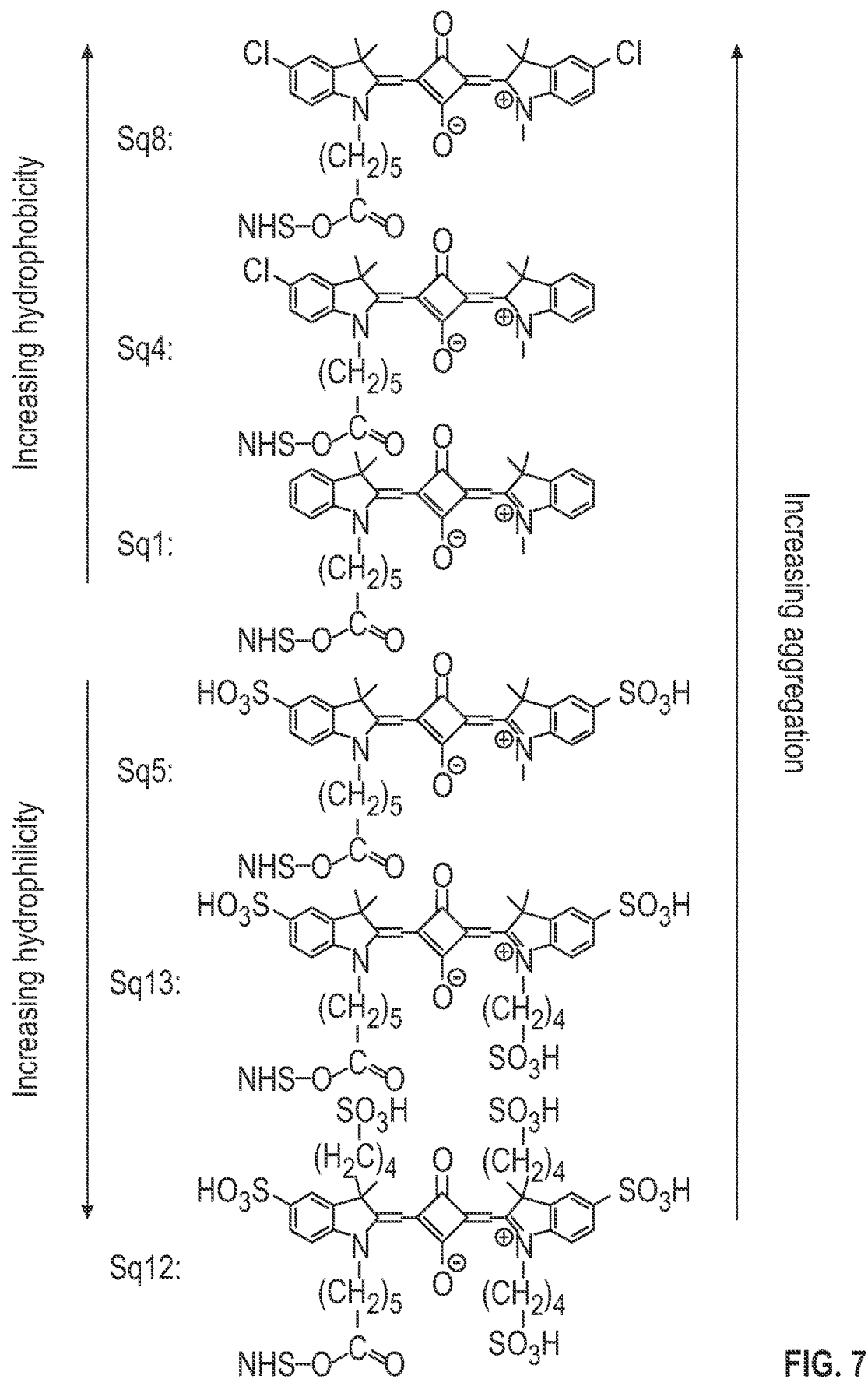
FIG. 7 is a schematic and graphical representation showing that by adding various substituents to squaraine, the dye hydrophobicity can be adjusted as shown. Increasing dye hydrophobicity is expected to promote aggregation and increase $J_{m,n}$.

To understand how exciton delocalization is influenced by dye structure, dye hydrophobicity may be altered while monitoring $J_{m,n}$. As a non-limiting example, the squarine (SQ) structure-aggregate property relationship was used to test the alteration of hydrophobicity and its impact on $J_{m,n}$ was investigated. Greater dye hydrophobicity leads to an increased propensity for the dyes to aggregate in aqueous solution either homogeneously (i.e., self-aggregate) or heterogeneously (i.e., aggregation on DNA templates). This is likely due to the greater dye hydrophobicity promoting denser dye packing and larger $J_{m,n}$. Dye hydrophobicity can be controlled by varying the nature and number of substituents. For instance, as the number of atomic chlorine (Cl) substituents on an organic dye increase, the more hydrophobic the dye, which is expected to increase its propensity to aggregate in aqueous solution leading to increased excitonic coupling strength, $J_{m,n}$. Conversely, as the number of charged sulfonate ($SO_3^-$) substituents on an organic dye increase, the less hydrophobic the dye, which is expected to decrease its propensity to aggregate in aqueous solution and decrease the excitonic coupling strength $J_{m,n}$. FIG. 7 shows a series of SQs that differ only in the number of atomic Cl and SO3− substituents: Sq8 (two Cl atoms), Sq4 (one Cl atom), Sq1 (neither a Cl atom nor a SO3−), Sq5 (SO3−), Sq13 (four SO3−), and Sq12 (five SO3−). It is possible to form heterodimers (e.g., Sq1-Sq5) to even more finely tune dye packing and $J_{m,n}$. Additionally, tuning dye hydrophobicity provide a means to vary the type of dye aggregate stacking; the greater the hydrophobicity, the greater the tendency to form H-aggregates (face-to-face). Conversely, the lesser the hydrophobicity, the greater the tendency to form J-aggregates (head-to-tail).

Influence of Dye Sterics on $\tau_p$ via $\Phi_F$

Excited-state (ES) quenching (i.e., small $\tau_p$) in dye aggregates (e.g., particularly in H-aggregates) is important to overcome to effectively utilize quantum entanglement. To circumvent small $\tau_p$, the dye structure will be modified to prevent H-aggregate packing, and limit dye-dye intermolecular motion (i.e., dye-dye sliding), which also facilitates ES quenching. Dye aggregates may be evaluated based on their $\Phi_F$, whose value is directly proportional to $\tau_p$; a higher $\Phi_F$ indicates suppressed nonradiative decay pathways and an increased $\tau_p$. The steric hindrance between dyes in a dye aggregate will circumvent H-aggregation, limit dye-dye intermolecular motion, and enhance $\Phi_F$ (and $\tau_p$). Similar to aggregates of cyanine dyes, SQ aggregates suffer from short ES lifetimes. When tethered to DNA, SQ aggregates also exhibit low $\Phi_F$, indicating short $\tau_p$. Incorporating a rotaxane ring around a SQ (i.e., a squaraine-rotaxane dye or SR) to protect the squarate bridge increases photochemical stability, modifies aggregation propensity, and increases $\Phi_F$ due to the steric effect of the rotaxane ring.

Figure 8E:
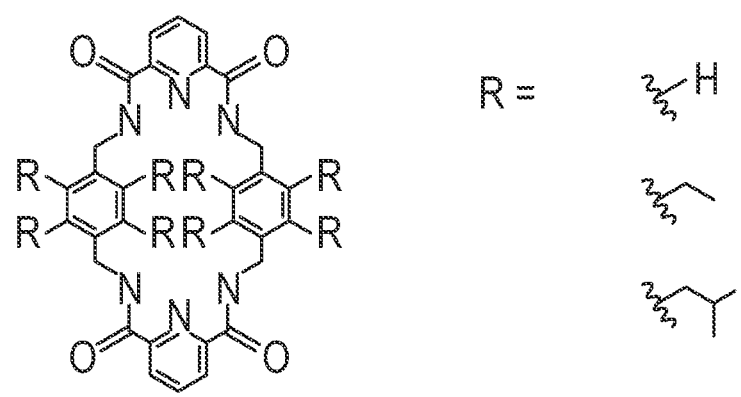
FIG. 8E is a schematic representation of the approach to vary steric bulk by changing rotaxane ring substituents.

The effect of steric hindrance in aggregates of SQs and SRs was investigated (FIG. 8A). In addition to improved dye properties, the rotaxane ring will also circumvent H-aggregation and limit intermolecular motion in DNA-templated dye aggregates (FIG. 8B), and thus suppress nonradiative decay and increase both $\Phi_F$ and $\tau_p$. When compared with Square-660-NHS, preliminary results on SeTau-670-NHS (also available via SETA BioMedicals) are promising—the dye aggregates exhibit strong electronic coupling, as is evident by Davydov splitting suggestive of an oblique packing arrangement, and appreciably less fluorescence quenching (FIG. 8C). Namely, while the fluorescence intensity of SQ aggregates is reduced by ~20× (compared with the dye monomer), that of the SR aggregates is reduced only by ~4×. Hence, rotaxanes suppress nonradiative decay in SQ aggregates in the following ways: (i) varying the number of rotaxane rings (i.e., SQ:SQ, SQ:SR, and SR:SR aggregates), and (ii) varying rotaxane ring substituent groups (FIGS. 8D and 8E). Greater steric hindrance will be achieved with more rings and longer and bulkier ring substituents. All of these effects limit dye-dye intermolecular motion, suppress nonradiative decay, and thus increase both $\Phi_F$ and $\tau_p$. There is also the potential that, with these structural changes, the distance between dyes in the aggregate will increase, potentially decreasing $J_{m,n}$. Hence, monitoring exciton delocalization of the SR dye aggregates will be necessary to ensure that $J_{m,n}$ is not significantly diminished. The samples exhibiting the largest $\Phi_F$, while still maintaining exciton delocalization, can then be provided to the ultrafast team to directly measure $\tau_p$.

Impact of Dye Asymmetry on $J_{m,n}$

Figure 9:
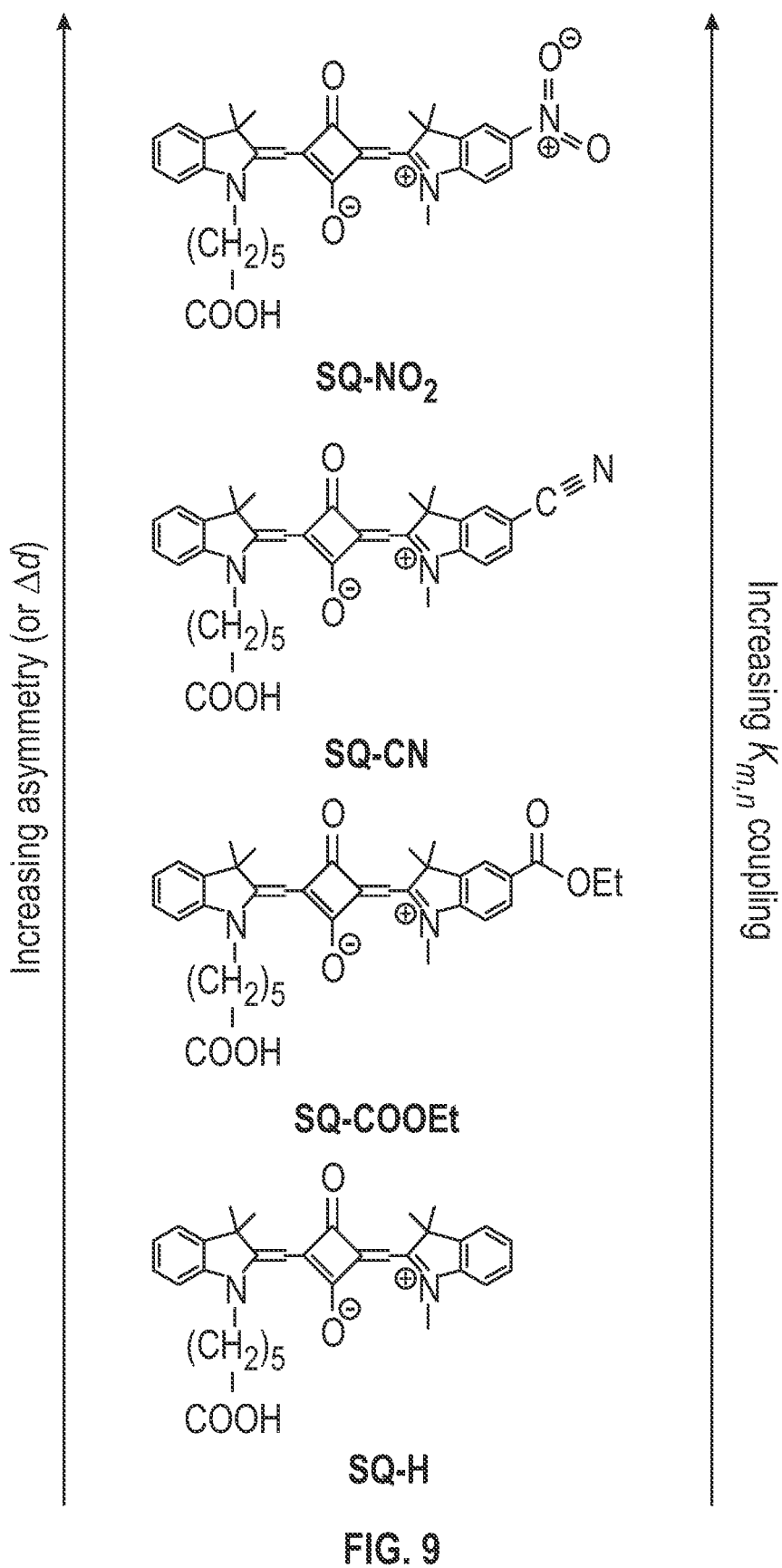
FIG. 9 is a schematic representation of a series of squaraine dyes with a substituent on one end with increasing electron withdrawing strength to increase dye asymmetry.

Short intermolecular dye distances (e.g. dense dye packing) and large µ and Δd will result in large $J_{m,n}$ and $K_{m,n}$ in dye aggregates. Increasing the electron withdrawing strength of a substituent on one side of the symmetric dye β-carotene strengthens the permanent molecular dipole. This chemical approach to inducing dye asymmetry was quantified via Stark absorption spectroscopy, with the most asymmetric β-carotene derivative exhibiting a Δd of ~40 D. Similar studies of asymmetry in cyanine dyes have revealed large changes in Δd. Modifying a dye's conjugated bond system to produce more asymmetric structures will yield dyes with greater Δd and dye aggregates with large $J_{m,n}$ and $K_{m,n}$. As shown in FIG. 9, the asymmetry of SQ dyes was altered starting with symmetric SQ-H, end substituents with increasing electron withdrawing strength, i.e., SQ-H<Sq-COOEt<Sq-CN<Sq-$NO_2$, were added.

To ensure that dye asymmetry does not inhibit $J_{m,n}$, the Davydov splitting in the steady state absorption spectrum is monitored. $\Phi_F$ will also be measured via steady state fluorescence to ensure that intersystem crossing, electron transfer, or excimer relaxation, which could quench the ES and lead to small $\tau_p$, are not promoted by increasing dye asymmetry. Obtaining CD spectra of the dye aggregates and simultaneously modeling the absorption and CD data via the modified KRM model analysis tool will provide stacking geometries (i.e., H- or J-type) and may simultaneously increase $J_{m,n}$ and $K_{m,n}$ and mitigate ES quenching.

Aggregate-Aggregate $J_{m,n}$ in Extended Dye Networks

Figure 10A:
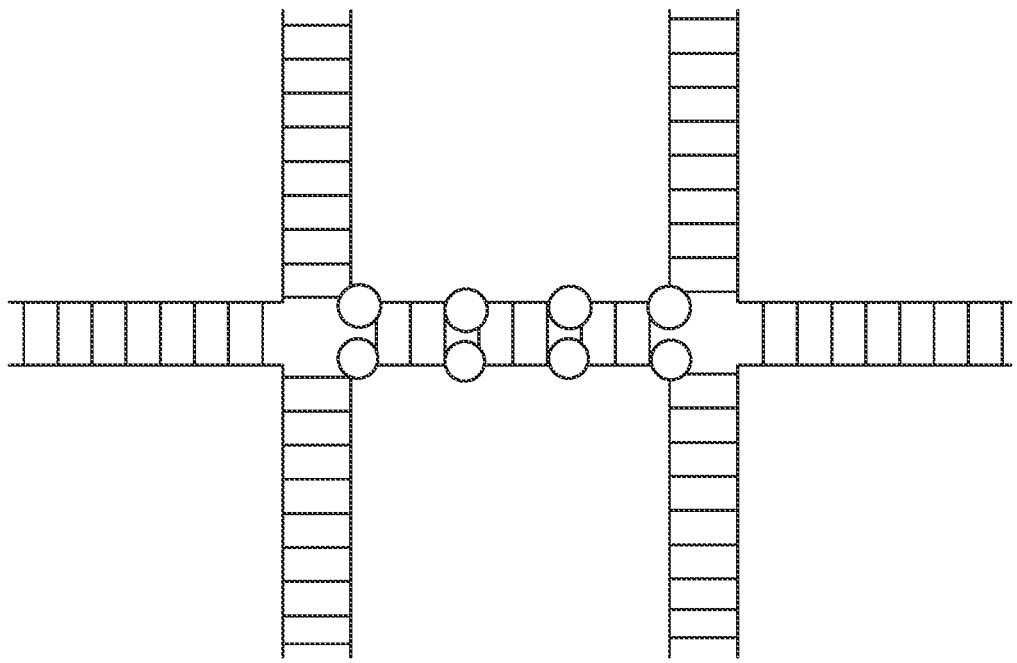
FIG. 10A is a schematic representation of a series of dimers (dots) organized by a multi-Holliday junction DNA array.
Figure 10B:
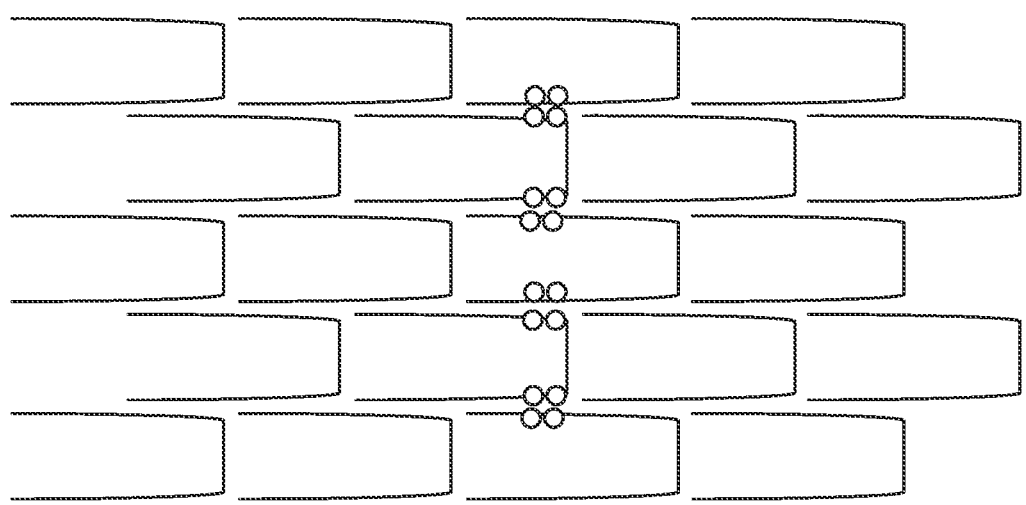
FIG. 10B is a schematic representation of a series of tetramers (dots) organized by a 2D DNA brick.

Exciton delocalization extending over more than two dyes is important to supporting multi-exciton entangled states. Creating higher order aggregate structures such as aggregates of dye aggregates may extended the range of exciton delocalization. Using dye aggregates with enhanced extinction coefficients, multiple configurations of aggregates of a dye aggregate (e.g., aggregate dimers, trimers, tetramers, etc.) may resemble an individual dye molecule with a very large extinction coefficient and that the coupling between aggregates (of aggregates) can be described by an effective $J_{m,n}$ where m and n are neighboring aggregates. FIG. 10A shows one such a configuration in which dye dimers are formed along the arm shared by two linked, immobile 4-arm Holliday junctions. FIG. 10B shows another approach in which dye tetramers are configured on a nucleic acid brick template.

Example 4—Parameter K

As discussed in Example 3, dyes with a large dye transition dipole moment (µ) and a large difference between the electronic ground-state and electronic excited-state static dipole (Δd), due to dye polarity (i.e., dye asymmetry), will result in large $J_{m,n}$ and $K_{m,n}$ for dye aggregates with small intermolecular distances (e.g. dense dye packing). It has been shown that increasing the electron withdrawing strength of a substituent on one side of the symmetric dye β-carotene strengthens the permanent molecular dipole making the dye asymmetric. The chemical approach to inducing dye asymmetry shoed the most asymmetric β-carotene derivative exhibiting a Δd of ~40 D. Similar studies of asymmetry in cyanine dyes have revealed large changes in Δd. By adding increasingly stronger electron withdrawing substituents to a symmetric dye to produce more asymmetric structures dyes with greater Δd and dye aggregates with large $J_{m,n}$ and $K_{m,n}$ may be generated. Cyanine dyes of the Cy5 class have been systematically altered with electron withdrawing end substituents to produce conjugated systems with increasing polarity as shown in FIG. 11. Starting with symmetric Cy5 and adding end substituents with increasing electron withdrawing strength, the Δd and $K_{m,n}$ in aggregates templated via Holliday junctions is altered.

Example 5—Parameter Jct

Jct (ct=charge transfer) is the coupling between dyes related to the overlap of the wavefunctions in the conjugated system. The distance between the adjacent dyes and their relative displacement controls the coupling. The greater the constructive overlap of the wavefunctions, the stronger the Jct. In general, the greater the steric hindrance, the less Jct. Hence, if the steric hindrance between the two adjacent dyes can be controlled, then Jct can be controlled or tuned.

As discussed in Example 3, the effect of steric hindrance in aggregates of SQs and SRs was investigated (FIG. 8A). In addition to improved dye properties, the rotaxane ring will also circumvent H-aggregation and limit intermolecular motion in DNA-templated dye aggregates (FIG. 8B), and thus suppress nonradiative decay and increase both $\Phi_F$ and $\tau_p$. When compared with Square-660-NHS, preliminary results on SeTau-670-NHS (also available via SETA Bio-Medicals) are promising—the dye aggregates exhibit strong electronic coupling, as is evident by Davydov splitting suggestive of an oblique packing arrangement, and appreciably less fluorescence quenching (FIG. 8C). Namely, while the fluorescence intensity of SQ aggregates is reduced by ~20× (compared with the dye monomer), that of the SR aggregates is reduced only by ~4×. Hence, rotaxanes suppress nonradiative decay in SQ aggregates in the following ways: (i) varying the number of rotaxane rings (i.e., SQ:SQ, SQ:SR, and SR:SR aggregates), and (ii) varying rotaxane ring substituent groups (FIGS. 8D and 8E). Greater steric hindrance will be achieved with more rings and longer and bulkier ring substituents. All of these effects limit dye-dye intermolecular motion, suppress nonradiative decay, and thus increase both $\Phi_F$ and $\tau_p$. There is also the potential that, with these structural changes, the distance between dyes in the aggregate will increase, potentially decreasing $J_{m,n}$. Hence, monitoring exciton delocalization of the SR dye aggregates will be necessary to ensure that $J_{m,n}$ is not significantly diminished. The samples exhibiting the largest $\Phi_F$, while still maintaining exciton delocalization, can then be provided to the ultrafast team to directly measure $\tau_p$.

In addition to using rings on dyes, such as the SR dyes, one skilled in the art would know that the addition of any long and/or bulky substituents will impact dye packing in single crystals and crystalline films. Further, chiral substituents are also possible to alter Jct as they perturb dye packing.

Example 6—Measurement of Additional Parameters

Figure 12:
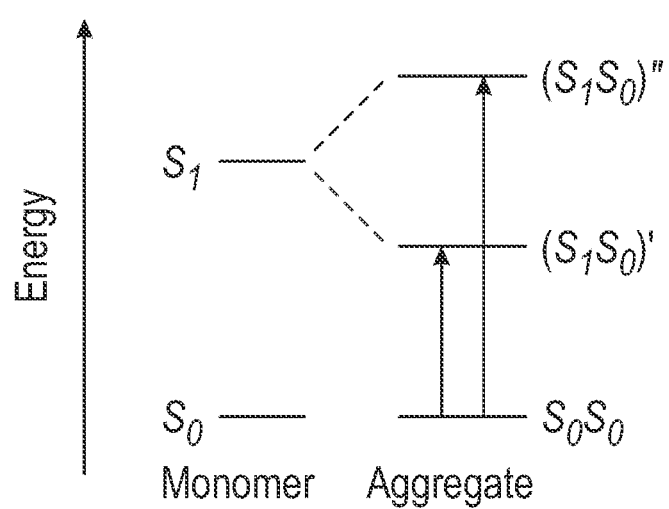
FIG. 12 is a schematic representation of Jablonski-type diagram indicating Davydov splitting and labeling of resultant states $(S_1S_0)'$ and $(S_1S_0)''$ important in excitonic quantum coherence. Associated optical transitions are indicated by black arrows.

Long coherence times and strong exciton-exciton interactions are important to effectively prepare and control entangled many-exciton states. Important in this regard is developing a better understanding of the underlying mechanisms of excited-state quenching (i.e., the relaxation pathway or pathways that determine the population lifetime, $\tau_p$) in excitonically coupled systems. $\tau_p$ directly impacts homogeneous coherence dephasing, Tc, via the following expression:

$$\frac{1}{\tau_c} = \frac{1}{2\tau_p} + \frac{1}{\tau_c^*}, \quad (9)$$

where $\tau_c^*$ is pure coherence dephasing. Further, while an optical coherence involves states that are directly optically accessible, i.e., the ground state $S_0S_0$ and terminating states, an excitonic coherence involves a superposition of low- and high-energy excitonic states, i.e., $(S_1S_0)'$ and $(S_1S_0)''$ (FIG. 12). In the absence of correlated bath fluctuations, we can expect:

$$\frac{1}{\tau_{c,<(S_1S_0)'|(S_1S_0)''>}} = \frac{1}{\tau_{c,<(S_0S_0)|(S_1S_0)'>}} + \frac{1}{\tau_{c,<(S_0S_0)|(S_1S_0)''>}} \quad (10)$$

Thus, much like how μ and Δd provide insights into $J_{m,n}$ and $K_{m,n}$, insights into exciton coherence dephasing can be gained by studying the optical coherences associated with $(S_1S_0)'$ and $(S_1S_0)''$. Because Tc is directly proportional to $\tau_p$, transient absorption spectroscopy may be used to measure $\tau_p$ of $(S_1S_0)'$ and $(S_1S_0)''$. It is also important to measure Tc of $(S_1S_0)'$ and $(S_1S_0)''$ and disentangle homogeneous and inhomogeneous contributions to spectral broadening (i.e., ΔEhomog and ΔEinhomog). Tc governs the homogeneous spectral width, ΔEhomog, via the following expression:

$$\Delta E_{homog} = \frac{1}{\pi \tau_c c}, \quad (11)$$

where ΔEhomog is expressed in units of wavenumber (cm⁻') In an ensemble, both ΔEhomog and the inhomogeneous spectral width, ΔEinhomog, play a role in coherence dephasing. Thus, various ultrafast nonlinear spectroscopies will be used to measure Tc associated with $(S_1S_0)'$ and $(S_1S_0)''$ transitions and disentangle ΔEhomog and ΔEinhomog contributions to ΔE. In addition to long coherence times, exciton-exciton interactions are important to effectively create and control entangled many-exciton states. Exciton-exciton interactions are mediated by the biexciton coupling element, $K_{m,n}$, which is directly proportional to the square of the difference static (i.e., permanent) dipole moment, Δd. Direct measurements of Δd via Stark spectroscopy of DNA-templated dyes and dye aggregates.

Figure 13A:
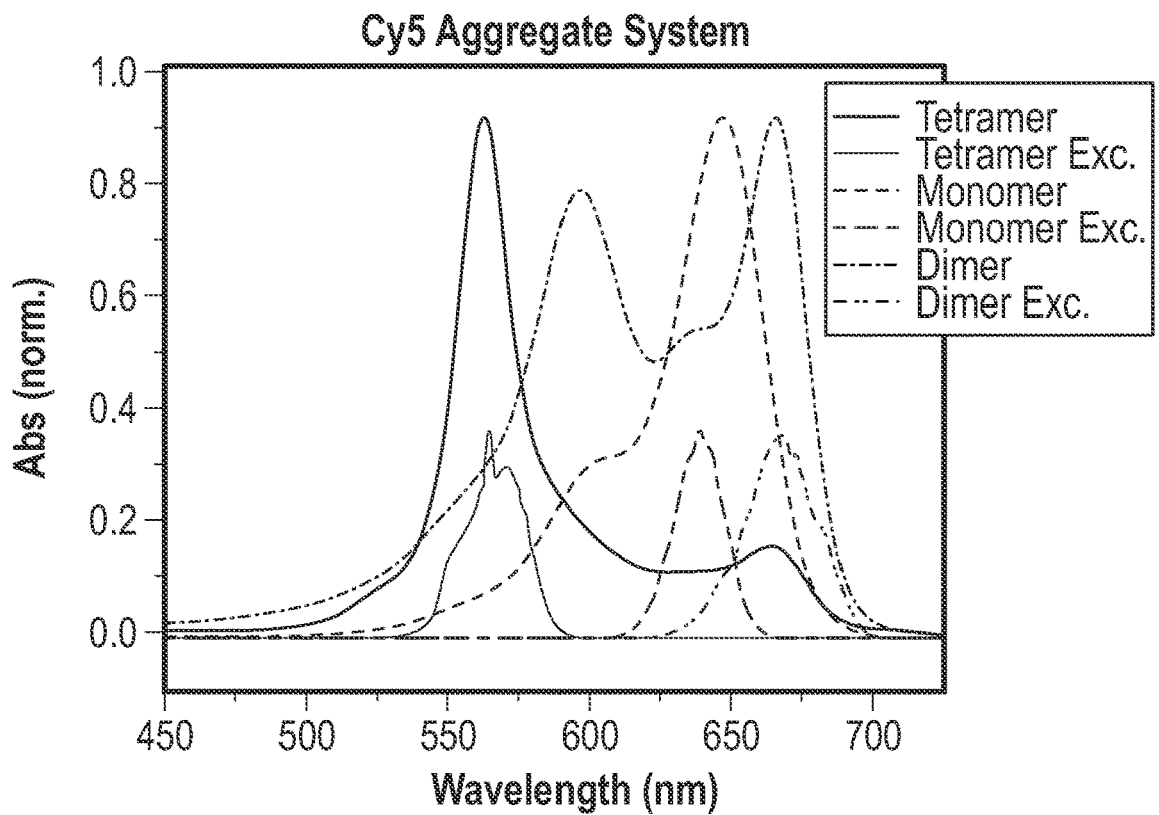
FIG. 13A is a graphical representation of the steady-state absorption and laser spectra of Cy5 monomer and aggregates.
Figure 13B:
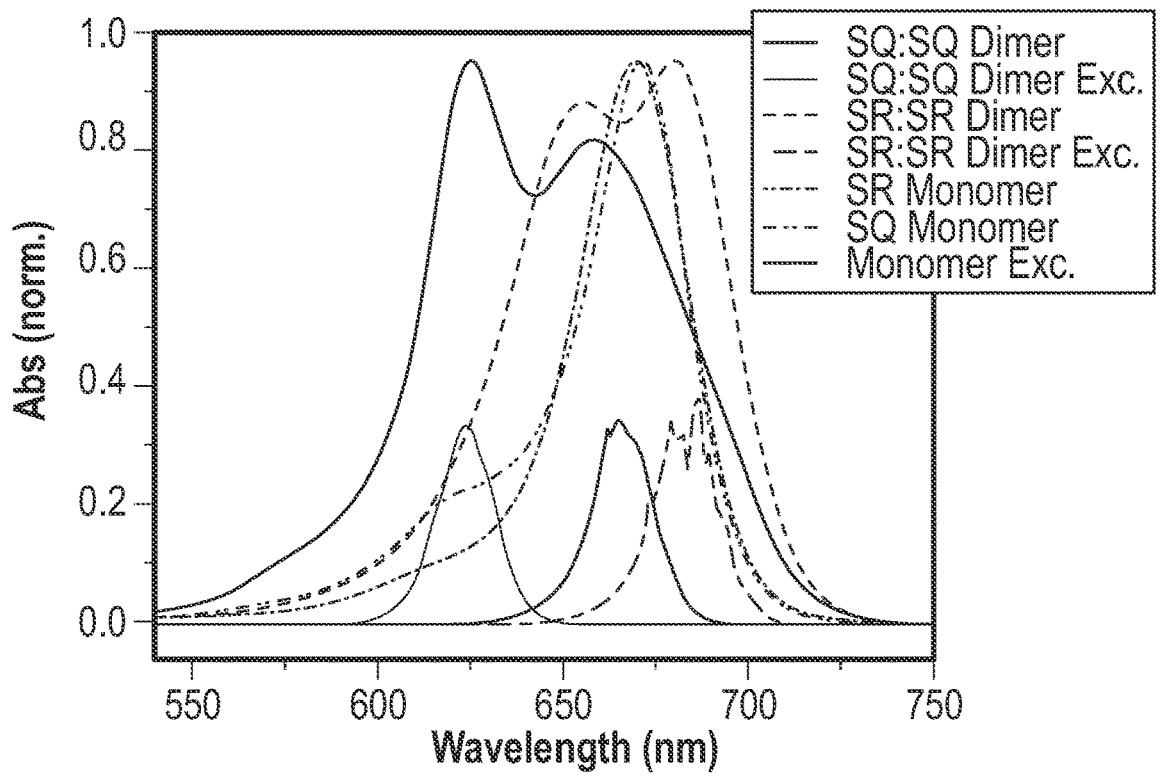
FIG. 13B is a graphical representation of the steady-state absorption and laser spectra for SQ and SR monomer and aggregates.
Figure 13C:
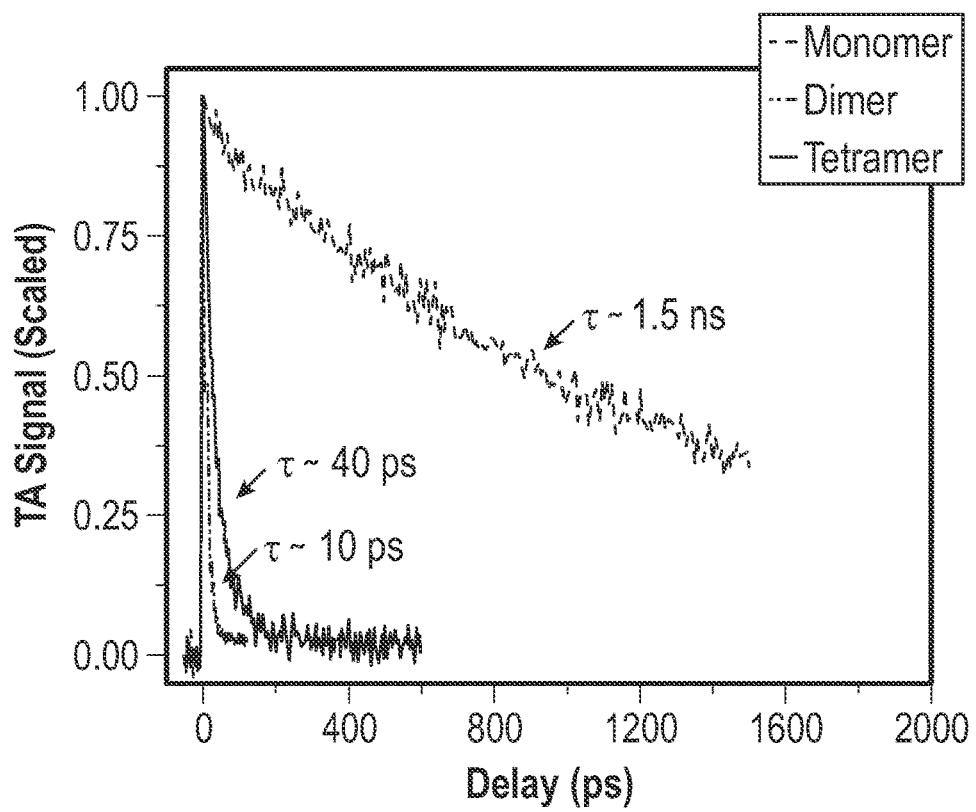
FIG. 13C is a graphical representation of the transient absorption kinetics of Cy5 monomer and aggregates.
Figure 13D:
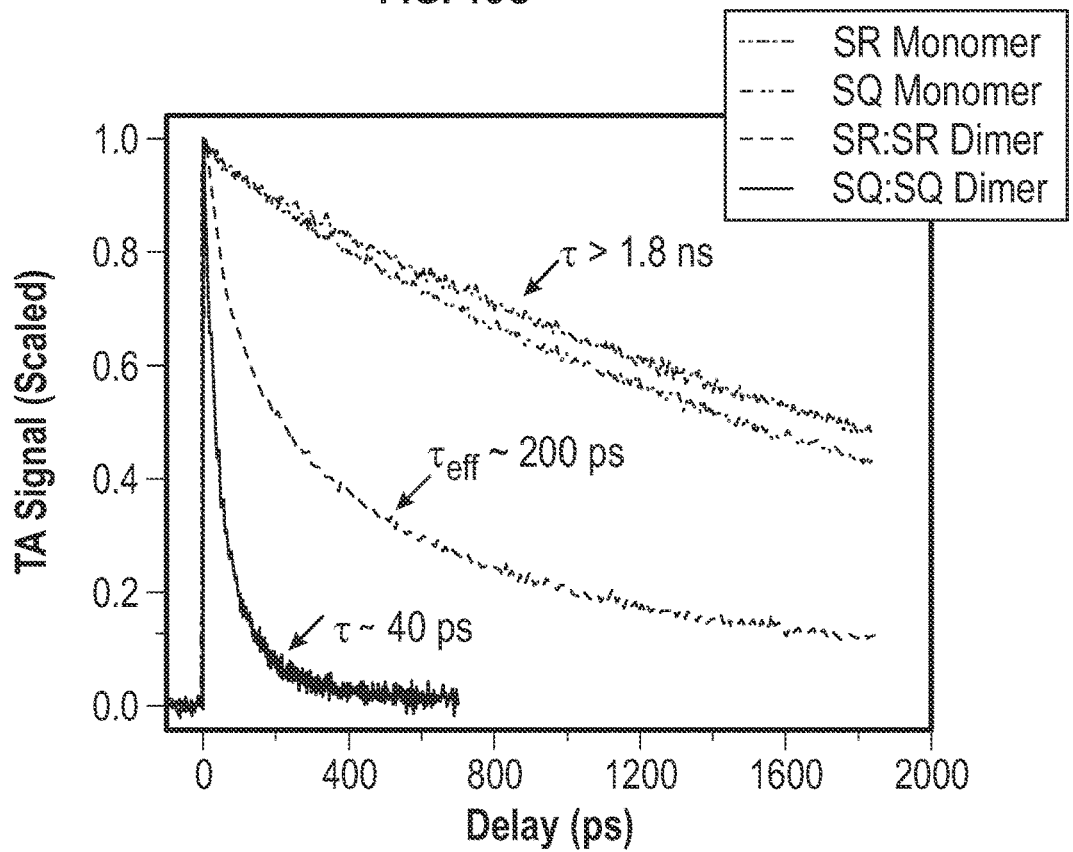
FIG. 13D is a graphical representation of the transient absorption kinetics for SQ and SR monomer and aggregates.

Transient Absorption Spectroscopy to Measure $\tau_p$, Excitor Delocalization, and Diffusion Because insights into the excitonic Tc can be gained by studying Tc of the constituent optical coherences, and because Tc is directly proportional to $\tau_p$, direct measurement, via femtosecond transient absorption (fs TA) spectroscopy (see FIGS. 8D, 8E), of the $\tau_p$ of the $(S_1S_0)'$ and $(S_1S_0)''$ states involved in the exciton superposition. Excited-state (ES) quenching, also called nonphotochemical quenching, is a general problem in molecular dye aggregates. ES quenching (i.e., small TO of $(S_1S_0)'$ in DNA-templated cyanine aggregates (FIGS. 3A and 13C) was identified. Similar ES quenching has been observed in DNA-templated SQ aggregates (see also FIG. 8C). To mitigate ES quenching (i.e., increase $\tau_p$), H-aggregate packing and limit dye-dye sliding by DNA-templating SR dye aggregates was sterically hindered. The increased steric bulkiness of constituent dyes in DNA-templated dye aggregates may increase if) of $(S_1S_0)'$. Increasing $J_{m,n}$ may also increase $\tau_p$ of $(S_1S_0)''$. The fs TA results are promising—while SQ aggregates exhibit drastically shortened $\tau_p$ (relative to the monomer), a considerably longer lifetime (factor of 5) is observed in SR aggregates (FIGS. 13C, 13D). These results provide microscopic and quantitative insights into the differences in $\tau_p$ responsible for the different relative $\Phi_F$ noted in FIG. 8C. $\tau_p$ of $(S_1S_0)'$ of the asymmetric dye aggregates prepared in Example 3 which may induce rapid ES decay via intersystem crossing, electron transfer, or excimer relaxation, and must therefore be monitored. In accordance with the energy-gap law, $\tau_p$ of $(S_1S_0)''$ is expected to increase exponentially with excitonic energy splitting, which is directly proportional to $J_{m,n}$.

Exciton delocalization extending over more than two dyes is needed to support multi-exciton entangled states. Fluence-dependent transient absorption measurements, a simple extension of the $\tau_p$ measurements highlighted above, may also be performed to estimate the extent of exciton delocalization. Fluence-independent kinetics indicate the exciton is delocalized over the entire dye network, while fluence-dependent kinetics (as is evident via an additional decay component at high fluence) indicates the exciton is delocalized over only some subset of dyes. In the latter case, a series of fluence-dependent fs TA kinetics (i.e. $\tau_p$ as a function of fluence) can be modeled to obtain the capture radius, an estimate of the extent of exciton delocalization. The diffusion constant for the exciton can also be derived. In the limit of resonance energy transfer, the diffusion constant is proportional to the square of the coupling between dyes in the extended dye network (i.e., $J_{m,n}$), thereby providing a secondary confirmation of the aggregate-aggregate $J_{m,n}$.

Quantify Exciton Delocalization and Diffusion

Exciton delocalization extending over more than two dyes is needed to support multi-exciton entangled states. Thus, extent of exciton delocalization in the extended dye networks constructed may be measured. Fluence-dependent transient absorption measurements, a simple extension of the $\tau_p$ measurements highlighted above, may be performed to estimate the extent of exciton delocalization. Fluence-independent kinetics indicate the exciton is delocalized over the entire dye network, while fluence-dependent kinetics (as is evident via an additional decay component at high fluence) indicates the exciton is delocalized over only some subset of dyes. In the latter case, a series of fluence-dependent fs TA kinetics (i.e. $\tau_p$ as a function of fluence) can be modeled to obtain the capture radius, an estimate of the extent of exciton delocalization. The diffusion constant for the exciton can also be derived. In the limit of resonance energy transfer, the diffusion constant is proportional to the square of the coupling between dyes in the extended dye network (i.e., $J_{m,n}$), thereby providing a secondary confirmation of the aggregate-aggregate $J_{m,n}$.

Figure 14A:
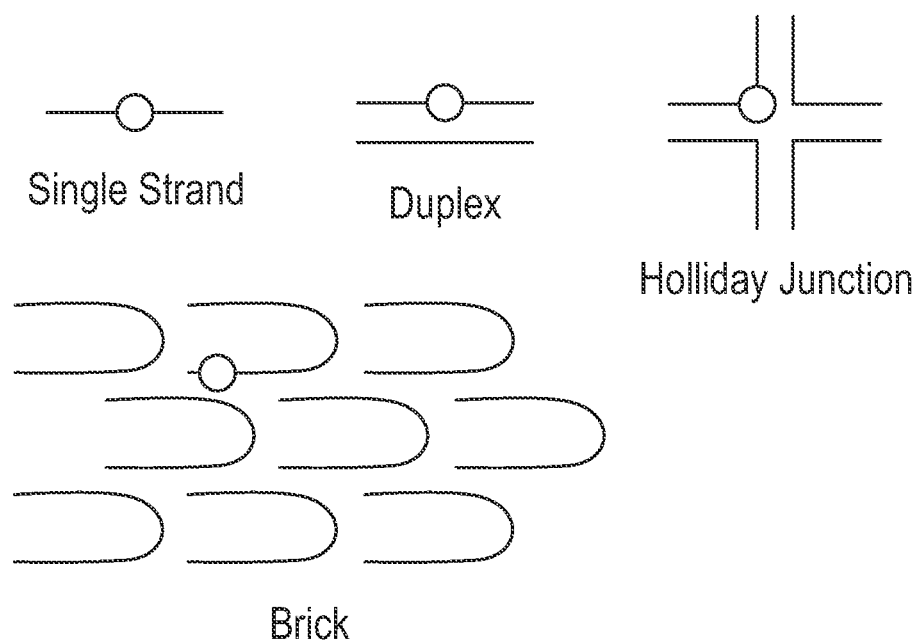
FIG. 14A is a schematic representation of DNA nanostructures of increasing complexity.
Figure 14B:
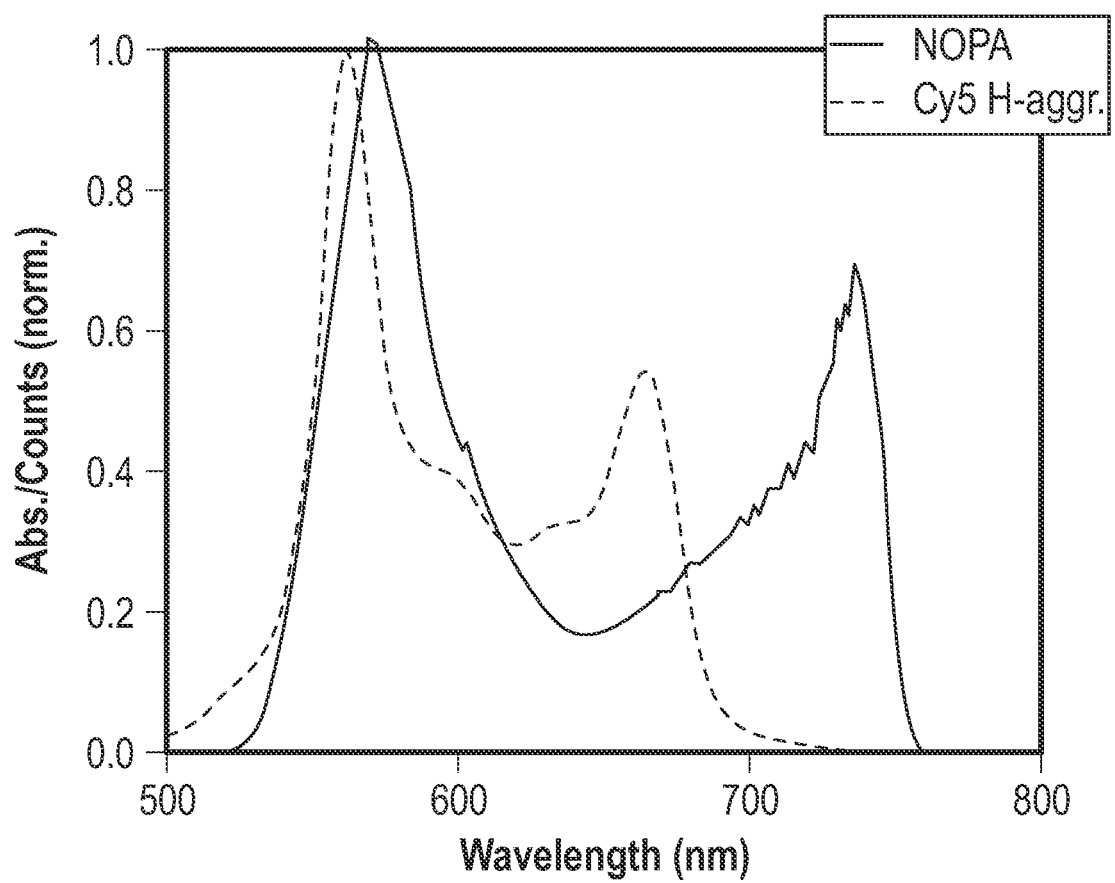
FIG. 14B is a graphical representation of the NOPA spectrum overlaid on the absorption spectrum of DNA-templated (H-type) cyanine aggregates.
Figure 15A:
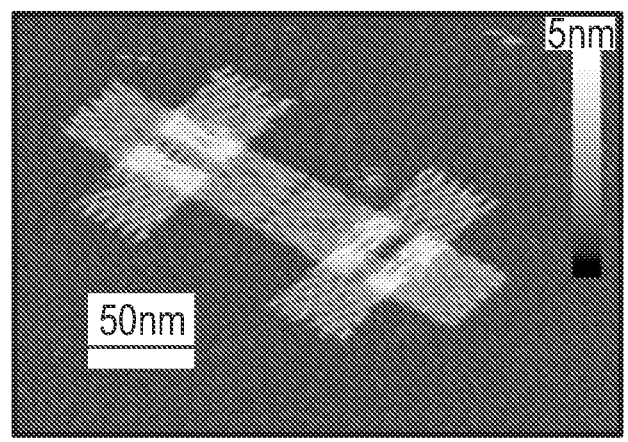
FIG. 15A is a pictorial representation of an atomic force micrograph of a single-molecule imaging platform consisting of two DNA origami cross-tiles connected through sticky-end hybridization. The dye of interest is imbedded within one of the arms of a cross tile by conjugation to a staple strand.
Figure 15B:
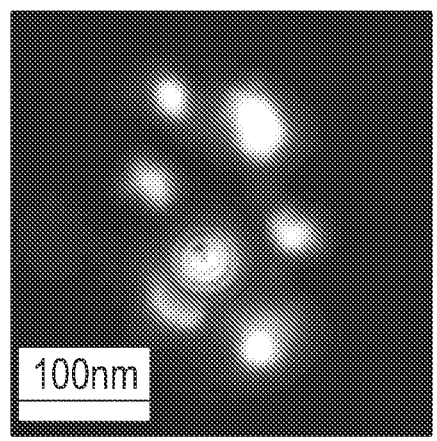
FIG. 15B is a pictorial representation of a super-resolution image of a DNA origami platform revealing the ends of the cross-tile arms (blue and orange spots). The imbedded dye (Cy5) orientation is determined by fitting its defocused diffraction pattern (scaled fit shown in green).
Figure 15C:
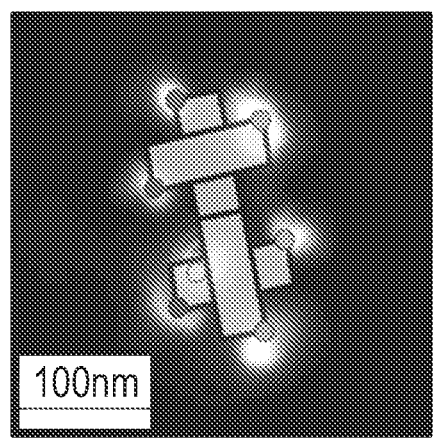
FIG. 15C is a schematic representation of a structural model superimposed on the super-resolved image of 15A and 15B.
Figure 15D:
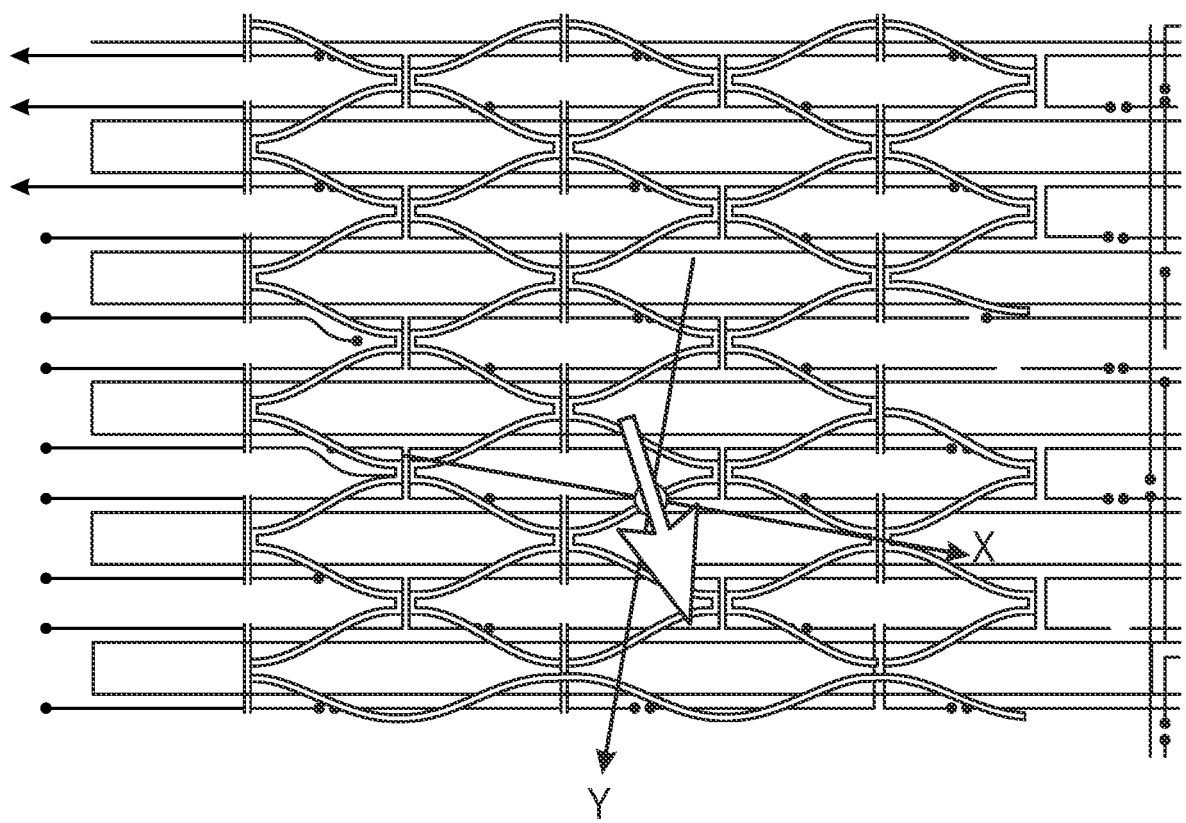
FIG. 15D is a schematic representation of the measured orientation of the dye's emission dipole within the weave of the DNA helices of the arm of the cross-tile origami. The emission dipole makes an angle of 35° with respect to the surface normal and an angle of 77° relative to the average helical axis (~90° relative to the local duplex).

Use of Ultrafast Nonlinear Spectroscopy to Measure $\tau c$ and Disentangle Homogeneous and Inhomogeneous Broadening Long excitonic Tc is important in entanglement because it determines the number of times an exciton can be exchanged before coherence is lost. Excitonic Tc is related to optical Tc and $\Delta$Ehomog. $\Delta$Ehomog arises from energy-gap fluctuations caused by dynamical motion of the system and the environment. In an ensemble, both $\Delta$Ehomog and $\Delta$Einhomog play a role in coherence dephasing. $\Delta$Einhomog results from the distribution of static micro-environments (e.g., structural heterogeneity). It has recently been shown that DNA duplexes impart considerable inhomogeneity on templated molecular aggregates. These results are consistent with the results seen in dye packing in DNA duplexes is sensitive to: (i) buffer composition and DNA concentration, and (ii) local base pair sequence. Dye packing in higher-order, Holliday junction DNA nanostructures, in contrast, is not sensitive to these changes. DNA nanostructures of higher order, e.g., Holliday-junctions and DNA bricks, may enhance Tc and suppress both homogeneous and inhomogeneous broadening in dyes and dye aggregates. For ease of implementation, two-pulse photon echo (2PPE) measurements may first be employed, which can directly measure optical Tc, on a series of DNA nanostructures of increasing order i.e., single strand, duplex, Holliday junction, and bricks—embedded with a single dye monomer (FIG. 14A). Optical $\tau_c$ (and $\Delta$Ehomog) of $S_1$ of the dye monomer may become longer (and narrower) in higher order and/or more rigid DNA nanostructures. Next, 2PPE measurements on dye dimers incorporated into DNA duplexes, Holliday junctions, and bricks may be performed. Optical Tc of $(S_1S_0)'$ and $(S_1S_0)''$, which will provide insight into dephasing of the excitonic superposition between $(S_1S_0)'$ and $(S_1S_0)''$, to increase in higher order DNA nanostructures. Further, using a noncollinear optical parametric amplifier (NOPA) (FIG. 14B), two-dimensional electronic spectroscopy (2D ES) measurements to quantify and disentangle $\Delta$Ehomog and $\Delta$Einhomog contributions to $\Delta$E. For $S_1$ of dye monomers and $(S_1S_0)'$ and $(S_1S_0)''$ of dye dimers, smaller $\Delta$Ehomog in higher order DNA nanostructures may be obtained. These results can be compared directly with Tc as measured via 2PPE. Further, $\Delta$Einhomog may be reduced in higher order DNA nanostructures, and direct measurements are ultimately necessary to reach this conclusion.

Use of Stark Spectroscopy to Measure $\Delta d$ of Asymmetric Dyes and Dye Aggregates To control and utilize entanglement, it is important to understand exciton-exciton interactions. Exciton-exciton interactions can be quantified through the biexciton coupling term Km,n, which is related to the difference dipole moment, $\Delta d$. Analogous to how the magnitude of $J_{m,n}$ is proportional to $\mu 2$, the magnitude of $K_{m,n}$ is directly proportional to $(\Delta d)^2$. The magnitude and direction of $\Delta d$, which also impacts the magnitude of $K_{m,n}$, may both obtained via the Stark analysis. To modify $\Delta d_m$, DNA nanostructures having dyes whose chemical structure varied as outlined in Example 3 (FIG. 9) are assembled. Stark absorption spectroscopy to directly measure $\Delta d_m$ of these dyes may be used. Secondly, we will test the validity of the dipole approximation by measuring $\Delta d_A$ for DNA-templated dye aggregates, where the constituent monomers have large Mm. If the dipole approximation is valid, MA represents the vector sum of all the $\Delta d$'s of the monomers composing the aggregate.

Example 7—Single-Molecule Characterization of DNA-Templated Dyes and Aggregates

It is often difficult to quantify the precision with which the templated molecules can be positioned and oriented. For example, in protein crystallization, the measurements represent the average crystal structure of millions of individual molecules. Similarly, in typical absorption and fluorescence measurements, the ensemble average spectra are recorded and variations in local environments are reflected in spectral inhomogeneity. Thus, it is difficult to know whether the observed spectral features, such as peak position and width, represent intrinsic properties of a well-formed aggregate system or the average over a range of heterogeneous aggregate structures (i.e., ensemble of structural variants that survive the purification processes; e.g, typically not capable of removing DNA constructs with missing dyes).

Combined single-molecule/single-aggregate dipole imaging and super-resolution microscopy may be used to quantify positional and orientation control of the dye, relative to the DNA template, and to assess how dye and nucleic acid properties influence this control. Single molecule measurements enable statistical analysis of the distribution of observed structural and spectral features based on frequency histograms of individual measurements. The measurements reveal relationships between molecular orientation and dye packing, dye tethers, and scaffold rigidity, based on the constructs studied in. With dye orientations established and spectra measurements, the relationships between orientation, local environment (e.g., sequence), packing, tethers, and rigidity on the emission and absorption spectral heterogeneity of monomers and aggregates may be calculated and studied through time-dependent single-molecule measurements. These studies provide direct single-molecule correlations between the various dyes and aggregate structure and manifested excitonic properties, and these correlations are crucial to accurately understanding DNA-based quantum information systems.

Quantify DNA-Templated Single Dye Orientation Precision

A central requirement of DNA-templated dye-based quantum information systems is the ability to control the position and orientation of molecules conjugated to a DNA strand. Both the orientation and distance between dyes governs the excitonic couplings, J and K. Near digital control over distance with a resolution of 3.4 Å is provided by current oligonucleotide synthesis capabilities, which can provide dye molecules conjugated to DNA with high yield at specified locations within a sequence. However, almost all dyes are attached to the DNA strand with a single molecular tether, which provides a large degree of freedom relative to its attachment position. In solution, the tethered dyes may rotate about the conjugation point or may stabilize within a local energy minimum. As mentioned above, this behavior may be influenced by dye hydrophobicity and linker length. Even for the cyanine dyes (Cy3, Cy5, Cy5.5), which can be conjugated with two linkers (one at each end of the dye), there is a finite degree of freedom available to the dye. These factors are further compounded by the nature of hydrogen bonding, base stacking, and thermodynamic properties of the DNA duplex. While dyes may form stable structures within the major or minor grooves, the DNA duplex may be subject to spontaneous dissociation (breathing), which is significant (up to 50% open) at terminal ends and near nicks or junctions, as well as formation of unintended secondary structures. Thus, while conjugation chemistry can provide 3.4 Å control over relative position, the relative dye orientations are subject to many factors that are not well understood.

To directly test dye orientation, as well as to determine the DNA construct design and environmental factors that affect orientation control, the orientations of conjugated dye systems with single-molecule dipole imaging are characterized. When combined with DNA-PAINT based super-resolution microscopy, these correlated images enable direct measurement of dye orientation relative to the underlying DNA-template. As shown in FIG. 15, dyes of interest can be conjugated to the staple strands of a DNA origami nanostructure, which is then immobilized to a glass surface. Such structures can be used as single-molecule imaging platforms, where DNA-PAINT based super-resolution imaging reveals the orientation of the origami and defocused diffraction pattern imaging reveals the dye's emission dipole orientation. A well-defined emission dipole orientation indicates that the dye orientation is fixed, which is to be expected for Cy5, which has two tethers to the DNA backbone. Further analysis of these data sets provides absolute single-molecule orientation within the DNA template, including the weave structure of the double helices. The precision of this orientation control may be quantified by the statistical standard deviation of the orientation angles of multiple immobilized dyes. How dye packing, tethers, scaffold rigidity, and other factors (e.g., cation concentration) influence the orientation angles and their standard deviations will directly inform the ensemble studies, ultrafast studies, and computational modeling of the above Examples. The dyes and dye aggregates of interest include all systems studied as ensembles in the other Objectives.

Quantify Emission Spectra Variance of Dye Aggregates

Once the precision of orientation control is quantified, and the relationships between nucleic acid and environmental properties is established, the single-molecule emission spectra of the dyes and dye aggregates may be measured. These measurements correlate variations in emission spectra and spectral width (which contributes directly to ensemble spectral inhomogeneity) with the orientation precision and the influencing factors of dye packing, tether length, and scaffold rigidity, as well as sequence and cation concentration. In particular, the dominate influencing factors found through the above Examples will be examined to directly assess the impact on emission spectra and spectral width. The results of these measurements will inform the understanding of the origins of homogeneous and inhomogeneous contributions to spectral broadening studied which are important to exciton exchange. This understanding will provide insight into how the nucleic acid and environmental factors can be used to minimize and control broadening.

Example 8—Frenkel Molecular Exciton Theory and Computational Methods

To aid in the prediction of key parameters of interest and the interpretation of data, the KRM model to incorporate $K_{m,n}$ and $\Delta_m$ may be updated to improve predictions. Machine Learning (ML) models may be used to screen numerous dye candidates that can meet defined criteria. DFT and TD-DFT may preferably be performed to estimate $\mu$, $\Delta d$, $J_{m,n}$, $K_{m,n}$ and absorption spectra of the dyes selected by ML.

Incorporation of $K_{m,n}$ and $\Delta m$ to Modify KRM Model

The KRM model analysis tool used to extract structure information from absorbance and CD data will be upgraded. This data analysis tool is based on the KRM model Hamiltonian which is equivalent to the first two terms of Eqn. (1) but which also incorporates the effects of a single dominant vibronic mode. It enables a user to extract the monomer optical transition energy, $\varepsilon_m^e$, the vibron energy, $\varepsilon_{m,n}^v$, and displacement parameter $D_{m,n}$ for the dominant vibronic mode, the width of the absorbance peaks $\Delta E$, the exchange energies $J_{mn}$, and the positions of the dyes and the orientations of their transition dipole vectors. The KRM model analysis tool may be extended to include all the interactions of the augmented Frenkel model. These include the exciton-exciton interaction energies $K_{mn}$ (Eqns. 3) and the two-exciton single-site energies $\Delta_m$ (Eqn. 1). The model may also handle more than one vibronic mode per dye thereby enabling more accurate modeling of vibronic effects. In addition, the software may handle biexciton states. Currently the software simultaneously fits absorbance data and CD spectra for the case when the dye aggregates have a uniform random orientation such as when suspended in solution. The software may enable the calculation of transition probabilities when the dye orientation and the optical polarization are specified.

Chemical Structure-Properly Relationships Revealed

To effectively determine chemical structure-property relationships and guide experiments, high-throughput screening to numerous dye candidates is employed, which has the potential to match the criteria described in any of the above Examples. Machine learning techniques may be employed on the dye candidates to efficiently and effectively develop accurate descriptions of complex dye structures and their properties: extinction coefficient, transition dipole μ, and the difference between the excited state and ground state static dipoles Δd, $J_{m,n}$ and $K_{m,n}$. The estimation of Pearson's correlation coefficient r can quantify a correlation between any two given properties.

Machine learning (ML) is an effective method of data analysis that enables computer systems to learn from data without human bias. ML is also used to find trends or correlations in the data that are not readily discovered by human intuition. In the field of materials science, ML techniques have significantly expedited the rate of materials discovery. Specifically, computational screening of new materials using conventional methods such as first-principles and atomistic modeling methods is time-consuming. Combining ML and modeling methods greatly reduces computational time and modeling uncertainty as well as increases the database size that can be processed in a short period of time.

Figure 16:
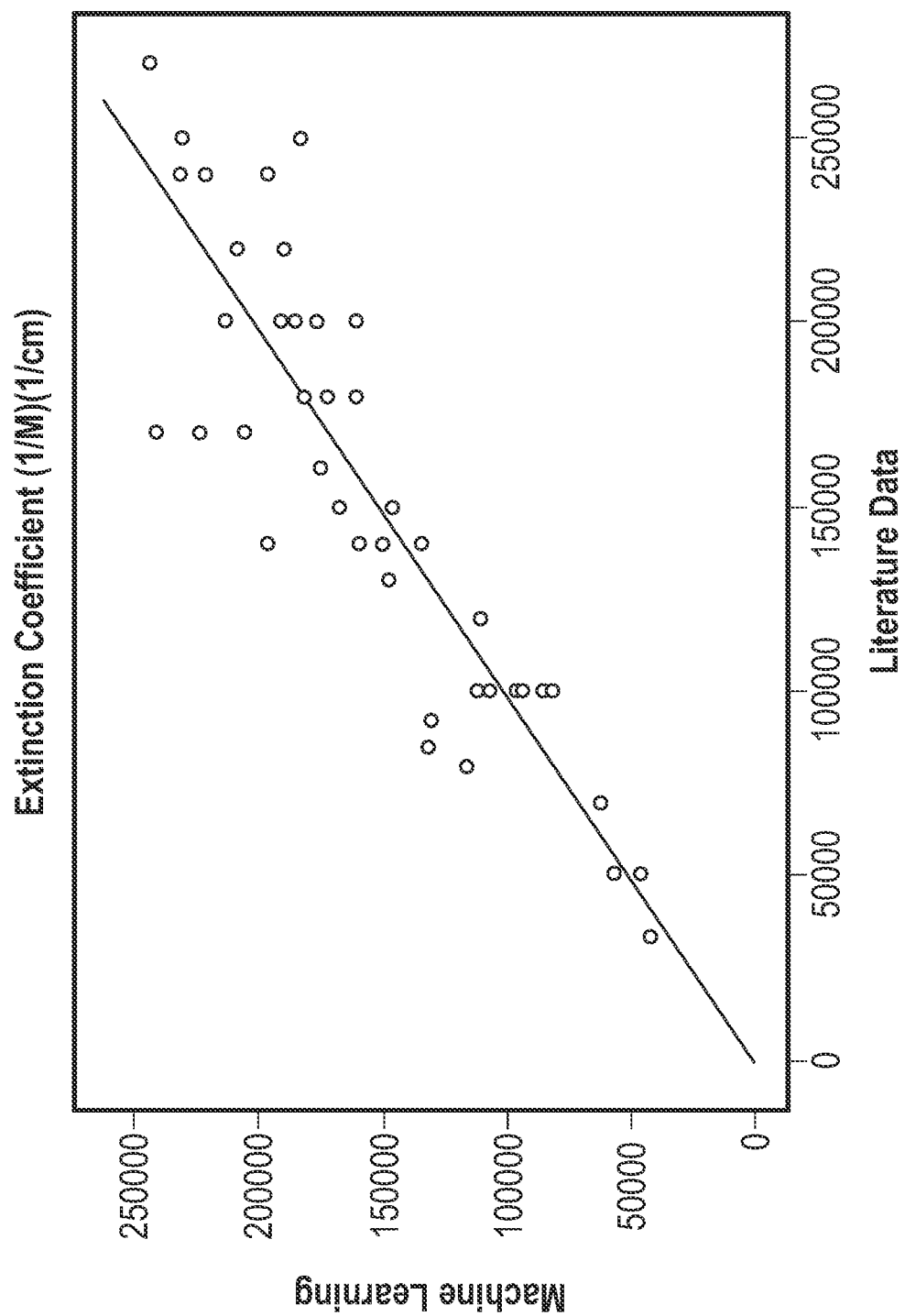
FIG. 16 is a graphical representation of the extinction coefficient predicted by random forest regression in comparison with literature with a prediction accuracy of 85%.

97 asymmetric dyes have been screened to explore their chemical structure-extinction coefficient relationships. Fingerprint vectors, i.e. structural descriptors, were generated based on chemical formula and dye structures, such as the number of CH3 groups, benzene rings, dye's conjugated bonds, heterocyclic rings, $SO_3^-$ groups, COOH groups, and dye linkers. Prediction accuracy of the ML model depended on the combination of fingerprint vectors, learning algorithms, and training datasets. All possible combinations of fingerprint vectors were tested to accurately determine the controlling structural features. This led to 114,688 models to test. Of the total 97 asymmetric dyes, 43 were chosen to be in the training set while the remaining dyes were reserved for the test set. A random forest regression ML algorithm was applied to each of 114,688 models to predict the extinction coefficients of asymmetric dyes. ML prediction accuracy reached 85% in comparison with literature data (FIG. 16). The number of CH3 groups, benzene rings, dye's conjugated bonds, and heterocyclic rings had the highest impact on extinction coefficient.

Larger datasets from published literature may be used in order to train, test, and validate the ML models. Dye properties such as hydrophobicity, sterics, tethers, the presence or absence of rotaxane, rotaxane functionalization, and nucleic acid properties (such as scaffold rigidity)—highlighted in the above Examples will be considered as fingerprint vectors in the ML models. Extinction coefficients of various dyes can be found in literature, but there is a paucity of data for transition dipole μ and the difference between the excited state and ground state static dipoles Δd, $J_{m,n}$ and $K_{m,n}$. DFT and TD-DFT to estimate the Δd, $J_{m,n}$ and $K_{m,n}$ values of dye candidates with relatively large extinction coefficients may be used. ML techniques may also be used to reveal the influence of structural features on those parameters and estimate feature importance to determine which structural features are dominant. Besides fingerprint vectors and training datasets, learning algorithms influence ML prediction accuracy. Other ML algorithms, such as Kernel Ridge Regression with Gaussian, Graph-based Kernels, and Neural Networks may alternately be used.

With given property datasets, we will evaluate their correlations through the calculation of Pearson correlation coefficient r, as below:

$$r = \sum_{i=1}^{n} (X_i - \overline{X})(Y_i - \overline{Y}) / \sqrt{\sum_{i=1}^{n} (X_i - \overline{X})^2} \sqrt{\sum_{i=1}^{n} (Y_i - \overline{Y})^2} \quad (11)$$

where $\{X_i\}$ and $\{Y_i\}$ are two given properties, such as $J_{m,n}$, $K_{m,n}$ or the extinction coefficient, E. n refers to the number of dye systems of interest. If r is close to 1, the two given properties are highly correlated.

Estimation of μ, Δd, $J_{m,n}$, $K_{m,n}$ and Absorption Spectrum Using Density Functional Theory (DFT) and Time Dependent Density Functional Theory (ID-DFT)

Estimates of II, Δd, $J_{m,n}$ and $K_{m,n}$ values, and absorption spectra (e.g. the width of the absorbance peaks ΔE) of the dyes selected using the above described machine learning will be obtained by DFT and TD-DFT. DFT is a computational quantum mechanical modeling method to study ground-state electronic structures of many-body systems. DFT calculations to optimize the ground-state geometries of the dyes as inputs for TD-DFT calculations may be performed. TD-DFT may be used to calculate the excited states of the dyes, providing excited-state geometries, excitation energies, and absorption spectra. Through a combination of DFT and TD-DFT, electronic static and transition dipole moments and absorption spectra may be calculated. Vibrationally resolved dipole moments and absorbance spectra will be obtained by Frank-Condon approximation.

Figure 17:
FIG. 17 is a schematic representation of a Cy5 dimer aggregate in dsDNA simulated using MD.

The use of the B3LYP hybrid functional along with the 6-31+G(d,p) of the Gaussian computational chemistry package provided computational results in good agreement with experiments. Dipole moment and extinction coefficient calculations using this functional were also time-effective and agreed well with literature. DFT may be used to optimize ground-state geometries, followed by TD-DFT for excited-state geometries. Through energy calculations in the ground and excited states we will acquire absorbance spectra and dipole moments. Calculations including solvent effects may be carried out for comparison. Through electronic absorption spectrum analysis and ground-state and excited-state calculations of dipole moments, DFT and TD-DFT results can be used to estimate $J_{m,n}$ and $K_{m,n}$ through Eqns. 2 & 3. $J_{m,n}$ and $K_{m,n}$ also depend on dye orientation. Molecular dynamics (MD) may be employed to simulate dye-DNA interaction in solvent. For atomic interactions, the CHARMM 36 force field may be employed with edits that include dye molecule parameters calculated by DFT. MD has been successfully demonstrated to determine dye orientation. FIG. 17 shows Cy5-Cy5 in the DNA at the temperature of 300 K. To verify the system has relaxed to equilibrium, the potential energy of the system and the root mean squared deviation value of the dye may be calculated. The dye orientation may be determined at each time step of the calculation after the system reaches the equilibrium state and the dye orientation factor, κ (related to Eqn. 2), will be calculated as:

$$\kappa = \mu_m \cdot \mu_n - 3(\mu_m \cdot R_{m,n})(\mu_n \cdot R^{m,n}) \qquad (12)$$

where $R_{m,n}$ is the unit vector pointing from the center of dye m to the center of dye n and $\mu_m$ and $\mu_n$ are the orientation unit vectors of dye m and dye n, respectively. The orientation vectors may be taken to be parallel to the main dye axes. Plotting the dye orientation as a function of separation will yield probability graphs that highlight the most probable dye configurations. These computational results may guide dye selection and synthesis. They can also serve as inputs for the KRM model and the augmented Frenkel model.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The inventions being thus described, it will be obvious that the same may be varied in many ways. Such variations are not to be regarded as a departure from the spirit and scope of the inventions and all such modifications are intended to be included within the scope of the following claims.

What is claimed:

1. A method of engineering parameter J, said parameter J being an excitonic hopping parameter or a measure of a coupling strength, of two or more dyes within one or more dye aggregates or between two or more dye aggregates, comprising:
    tuning the distance and/or an orientation between dyes and/or dye-to-dye intermolecular interactions; and
    using a nucleic acid architecture to in part control the tuning.

2. The method of claim 1, wherein the tuning of the dye-to-dye intermolecular interactions adjust one or more of hydrophobicity of the dye, symmetry, electronic factors, and/or sterics between one or more dyes.

3. The method of claim 2, wherein the intermolecular interactions adjusted is the hydrophobicity of the dye.

4. The method of claim 3, wherein the hydrophobicity is increased.

5. The method of claim 4, wherein a number of alkyl and/or Cl substitutes on the dye is increased.

6. The method of claim 3, wherein the hydrophobicity is decreased.

7. The method of claim 6, wherein a number of $SO_3^-$ substitutes on the dye is increased.

8. The method of claim 2, wherein a steric hindrance between one or more dyes is tuned.

9. A method of engineering parameter J, said parameter J being an excitonic hopping parameter or a measure of a coupling strength, of two or more dyes within one or more dye aggregates or between two or more dye aggregates, comprising:
    tuning the distance and/or orientation between dyes and/or dye-to-dye intermolecular interactions; and
    using a nucleic acid architecture to in part control the tuning;
    wherein a rotaxane ring and/or macrocycle is incorporated around or encapsulating one or more dyes.

10. A method of engineering parameter J, said parameter J being an excitonic hopping parameter or a measure of a coupling strength, of two or more dyes within one or more dye aggregates or between two or more dye aggregates, comprising:
    tuning the distance and/or orientation between dyes and/or dye-to-dye intermolecular interactions; and
    using a nucleic acid architecture to in part control the tuning;
    wherein a rotaxane ring and/or macrocycle is incorporated around or encapsulating one or more dyes;
    wherein the rotaxane ring and/or macrocycle is further substituted.

11. The method of claim 1, further comprising tethering one or more dye aggregates to a nucleic acid architecture.

12. The method of claim 11, wherein one or more dyes in the one or more dye aggregates is tethered by more than one tether and/or tethers of different lengths.

13. The method of claim 8, wherein a number and length of alkyl substituents incorporated on the dye is increased.

* * * * *